(12) United States Patent
Jablonski et al.

(10) Patent No.: US 9,149,426 B2
(45) Date of Patent: Oct. 6, 2015

(54) NANOPARTICLE COMPOSITION AND METHODS TO MAKE AND USE THE SAME

(71) Applicants: Monica Jablonski, Memphis, TN (US); Mallika Palamoor, Memphis, TN (US)

(72) Inventors: Monica Jablonski, Memphis, TN (US); Mallika Palamoor, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 13/767,734

(22) Filed: Feb. 14, 2013

(65) Prior Publication Data
US 2013/0209566 A1    Aug. 15, 2013

Related U.S. Application Data

(60) Provisional application No. 61/599,075, filed on Feb. 15, 2012.

(51) Int. Cl.
*A61K 9/00* (2006.01)
*A61K 31/715* (2006.01)
*A61K 31/635* (2006.01)
*A61K 31/137* (2006.01)
*A61K 38/38* (2006.01)
*A61K 9/51* (2006.01)
*B82Y 5/00* (2011.01)

(52) U.S. Cl.
CPC ............ *A61K 9/0048* (2013.01); *A61K 9/0051* (2013.01); *A61K 9/5153* (2013.01); *A61K 31/137* (2013.01); *A61K 31/635* (2013.01); *A61K 31/715* (2013.01); *A61K 38/385* (2013.01); *A61K 9/0019* (2013.01); *B82Y 5/00* (2013.01); *Y10S 977/773* (2013.01); *Y10S 977/906* (2013.01)

(58) Field of Classification Search
CPC .......................... A61K 31/715; A61K 9/0048
See application file for complete search history.

(56) References Cited

U.S. PATENT DOCUMENTS

| | | | |
|---|---|---|---|
| 6,117,454 A * | 9/2000 | Kreuter et al. ............... | 424/490 |
| 8,092,825 B2 | 1/2012 | Jablonski | |
| 8,257,743 B2 | 9/2012 | Yoo et al. | |
| 2007/0184068 A1* | 8/2007 | Renner et al. ............ | 424/204.1 |
| 2008/0038361 A1 | 2/2008 | Cheon et al. | |
| 2009/0060980 A1* | 3/2009 | Jablonski ..................... | 424/428 |
| 2009/0226531 A1* | 9/2009 | Lyons et al. ................. | 424/501 |

OTHER PUBLICATIONS

Wagh, V.D.; Inamdar, B.; Samanta, M.K. "Polymers used in ocular dosage form and drug delivery systems" Asian J Pharm 2008, 2, 12-17.*

Djakovic, L.; Dokic, P.; Radivojevic, P. "Investigation on the particle size distribution of O/W emulsions" Kolloid-Z. u. Z. Polymere 1971, 244, 324-332.*
Wagh, V.D.; Inamdar, B.; Samanta, M.K. "Polymers used in ocular dosage form and drug delivery systems" Asian J Pharm 2008, 2, 12-17.*
Drugs.com "Epinephrine" (www.drugs.com/ppa/epinephrine.html) accessed Jan. 27, 2014.*
Nile Red—Product data sheet (http://www.enzolifesciences.com/fileadmin/reports/els_a7805343b8.pdf) accessed Jan. 27, 2014.*
Helenius, A.; Aebi, M. "Intracellular Functions of N-Linked Glycans" Science 2001, 291, 2364-2369.*
Heller, J.; Barr, J.; Ng, S.Y.; Abdellauoi, K.S.; Gurny, R. "Poly(ortho esters): synthesis, characterization, properties and uses" Adv. Drug Del. Rev. 2002, 54, 1015-1039.*
Panyam, J. et al. "Polymer degradation and in vitro release of a model protein from poly(D,L-lactide-co-glycolide) nano- and microparticles" J. Control. Release 2003, 92, 173-187.*
Schwach-Abdellaoui, K; Heller, J.; Gurny, R. "Hydrolysis and Erosion Studies of Autocatalyzed Poly(ortho esters) Containing Lactoyl-Lactyl Acid Dimers" 1999, 32, 301-307.*
Suzanne Einmahl et al., A New Poly(Ortho Ester)-Based Drug Delivery System as an Adjunct Treatment in Filtering surgery,Investigative Ophthalmology & Visual Science, Mar. 2001, vol. 42, No. 3,Association for Research in vision and ophthalmology.
Bala I, Hariharan S, Kumar MN.; PLGA nanoparticles in drug delivery: the state of the art, Critical Reviews in Therpeutic Drug Carrier Systems, 21, 2004, 387-422.
Cohen-Sela, E.; Chorny, M. ; Koroukhov,; Danenberg, H. D. ; Golomb, G, A new double emulsion solvent diffusion technique for encapsulating hydrophilic molecules in PLGA nanoparticles, jthenal of controlled release, 133, 2009, 90-95.
Einmahl, S.; Behar-Cohen, F.; D'Hermies, F.; Rudaz, S.; Tabatabay, C.; Renard, G.; Gurny, R. A new poly(ortho ester)-based drug delivery system as an adjunct treatment in filtering surgery, Investigative Ophthalmology and Visual science, 2001, 42, 695-700.
Heller, J. Ocular delivery using poly(orthoesters), Advanced Drug Delivery Reviews, 2005, 57, 2053-2062.
Jablonski MM and Iannaccone A. (2001) Lactose Supports Müller Cell Protein Expression Patterns in the Absence of the Retinal Pigment Epithelium. Mol. Vis. 7:27-35.

(Continued)

*Primary Examiner* — Sean Basquill
*Assistant Examiner* — Andrew S Rosenthal
(74) *Attorney, Agent, or Firm* — Stites & Harbison PLLC; Cong Ding

(57) ABSTRACT

The present invention provides a novel nanoparticle drug delivery system generated from poly(ortho ester) polymers with sustained drug release capability and can be functionalized to allow for systemic delivery to various organ systems throughout the body. One important aspect of this invention is that the nanoparticle drug delivery system generated from poly(ortho ester) polymers encapsulate several types of drugs in poly(ortho ester) nanoparticles, including but not limited to lipophilic, hydrophilic small and large molecules and also hydrophilic and lipophilic dyes by adopting appropriate emulsion techniques. These poly(ortho ester) nanoparticles are biodegradable, biocompatible and controlled release drug delivery system with zero order kinetics, which can be used in various biomedical applications such as eye-related diseases, cancer, arthritis, etc.

28 Claims, 16 Drawing Sheets
(8 of 16 Drawing Sheet(s) Filed in Color)

(56) References Cited

OTHER PUBLICATIONS

K. Schwach-Abdellaoui, J. Heller, R. Gurny, Macromolecules, 1999, 32, 301.

K.Schwach-Abdellaoui, J. Heller, R. Gurny, Jthenal of Biomaterial Science Polymer Edn. 1999, 10, 375.

Ng, S. Y.; Shen, H. R.; Lopez, E.; Zherebin, Y.; Barr, J.; Schacht, E.; Heller, J. Development of a poly(orthoester) prototyoe with a latent acid in the polymer backbone for 5-fluortheacil delivery. J. Control. Release 2000, 65, 367-374.

Palamoor, M. and M.M. Jablonski, Poly(ortho ester) Nanoparticle-Based Targeted Intraocular Therapy for Controlled Release of Hydrophilic Molecules. Molecular pharmaceutics, 2013.

Rothen-Weinhold, A.; Schwach-Abdellaoui, K.; Barr, J.; Ng, S. Y.; Shen, H. R.; Gurny, R.; Heller, J. Release of BSA from poly(ortho ester) extruded thin strands, Jthenal of controlled Release, 2001, 71, 31-37.

Schwach-Abdellaoui, K.; Loup, P.; Vivien-Castioni, J.; Mombelli, N.; Baehni, A.; Barr, P.; Heller, J.; Gurny, R.; Bioerodible Injectable Poly(ortho ester) for Tetracycline Controlled Delivery to Periodontal Pockets: Preliminary Trial in Humans, AAPS pharmaceutical science, 4, 2002, 1-7.

Song, K. C. ; Lee, H. S. ; Choung, I. Y. ; Cho, K. I. ; Ahn, Y. ; Choi, E. J.; The effect of type of organic phase solvents on the particle size of poly(D, L-Lactide-co-glycolide) nanoparticles, Colloids and surfaces A: Physiochemical Engineering Aspects, 276, 2006, 162-167.

* cited by examiner

Rabbit 1105 before intravitreal injection    Rabbit 1105 14 days after intravitreal injection Rabbit M90 before intravitreal injection    Rabbit M90 after injection of 100nM NA3

Rabbit M80 3 days after injection of 1nM NA3    Rabbit M82 1 day after injection of 100nM NA3

Rabbit M90 7 days after injection of 100nM NA3

Blue=nuclei
Red=GFAP
Green=TUNEL

Rabbit 1108 before intravitreal injection      Rabbit 1108 14 days after intravitreal injection Rabbit 1101 before intravitreal injection    Rabbit 1101 14 days after injection of 10mg/ml NPs Rabbit 1108 before intravitreal injection    Rabbit 1108 3 days after injection of 10mg/ml Rabbit 1107 1 day after injection of 10mg/ml NPs    Rabbit 1108 14 day after injection of 10mg/ml NPs Blue=nuclei
Red=GFAP
Green=TUNEL

NANOPARTICLE COMPOSITION AND METHODS TO MAKE AND USE THE SAME

RELATED APPLICATIONS

This application claims priority under 35 USC Section 119(e) to U.S. patent application No. 61/599,075 filed on Feb. 15, 2012 (hereby specifically incorporated by reference in its entirety).

STATEMENT REGARDING FEDERALLY SPONSORED RESEARCH OR DEVELOPMENT

None.

FIELD OF INVENTION

The present invention relates to a novel nanoparticle composition and methods to make a nanoparticle-based drug delivery system. More particularly, the present invention relates to a nanoparticle-based drug delivery system generated from poly(ortho ester) polymers which have sustained drug release capability for the treatment of intraocular diseases.

BACKGROUND OF THE INVENTION

Atrophic age-related macular degeneration (AMD) affects more than 9 million individuals in the United States. With the increased longevity of the US population, this number will increase to ~17.8 million by 2050. The economic burden is estimated at ~$25 billion in lost gross domestic product. In 2004, the direct medical cost of age related macular degeneration treatment was estimated to be $575 million, excluding nursing home costs, productivity losses, and home health care costs.

Diabetic retinopathy is another leading cause of new cases of legal blindness among adults aged 20 to 74 years in the United States. The estimated prevalence of diabetic retinopathy and vision-threatening diabetic retinopathy was 28.5% and 4.4% among US adults with diabetes, respectively. Diabetes-related blindness is a personal catastrophe to the individual and costs the United States approximately $500 million annually. The development of a sustained release delivery system would expand the list of therapies that could be utilized to treat several chronic intraocular diseases including age related macular degeneration and diabetic retinopathy.

Glaucoma is the second leading cause of blindness in the world, according to the World Health Organization. Approximately 120,000 are blind from glaucoma, accounting for 9% to 12% of all cases of blindness in the United States. In terms of Social Security benefits, lost income tax revenues, and health care expenditures, the cost to the U.S. government is estimated to be over $1.5 billion annually.

Leber congenital amaurosis (LCA) is a rare, hereditary disorder that leads to retinal dysfunction and visual impairment at an early age, often from birth. Of all the retinal degenerations, it has the earliest age of onset and can be the most severe. The birth prevalence of LCA is two to three per 100,000 births. LCA accounts for the cause of blindness in more than 20% of children attending schools for the blind.

The development of a sustained release delivery system would expand the list of therapies that could be utilized to treat several chronic intraocular diseases such as, age related macular degeneration, diabetic retinopathy, glaucoma, Leber congenital amaurosis, etc.

Efficacious drug delivery to chronic diseases and disorders can be limited by dosing frequency. For example, drug delivery to the posterior segment of the eye is inherently limited by barriers created by the structures of the eye (e.g., the thick scleral tunic, absorption of the drops by the conjunctival and nasal vasculature, tight junctions between retinal pigment epithelium cells). The most direct route for administration of therapeutic drugs to the tissues in the back of an eye is via intravitreal injections. However, this route is limited by frequent need for repeat dosages, which can cause complications, such as endophthalmitis and retinal detachment. It would be ideal to have an injectable biodegradable device made of non-toxic materials that offered many advantages, such as an increase in the half-life of the drug, no need for removal of an implant and circumvention of the first-order kinetics of drug delivery that are experienced following injection of the drug alone (i.e., rapid rise in drug concentration followed by a rapid decrease).

There are several modes by which drugs can be administered to the posterior segment of the eye including systemic circulation, eye drops, transcleral delivery or intraocular injections. Systemic circulation, eye drops, and transcleral delivery methods are limited by barriers created by the structures of the eye (e.g., the thick scleral tunic, absorption of the drops by the conjunctival and nasal vasculature, tight junctions between retinal pigment epithelium cells). Therefore, intravitreal injection is the safest and most effective route for administration of therapeutic drugs to the target tissues of the back of the eye, especially the retina. However, it is critical to limit the number of repeated injections to minimize the risk of infection or retinal detachment.

A nanoparticle drug delivery system has many technological advantages such as longer shelf life, ability to carry both hydrophilic and lipophilic substances, and high drug loading capacity. Nanoparticles can also be designed to allow sustained drug release from the particulate system in the treatment of chronic diseases in order to enable reduction of dosing frequency in certain drugs. Drug-loaded nanoparticles constitute a versatile drug delivery system and have the ability to overcome physiological barriers and guide the drug to specific cells or intracellular compartments either by passive or ligand-mediated targeting mechanisms.

For ophthalmic applications, biodegradable polymer, poly (ortho ester) have been used as bolus drug depots. Poly(ortho ester)s are hydrophobic polymers, degraded by surface erosion confined to the polymer-water interfaces following zero-order drug release kinetics when placed in a biological environment. The erosion rate of a poly(ortho ester) polymer is controlled by the incorporation of a latent acid such as lactic acid (LA), resulting in a $4^{th}$ generation poly(ortho ester) polymer (poly(ortho ester) IV) (Schwach-Abdellaoui, K.; Heller, J.; Gurny, R. *Hydrolysis and erosion studies of autocatalyzed poly(ortho esters) containing lactoyl-Lactyl acid dimers, Macromolecules* 1999, 32, 301-307). While poly(ortho ester)s have been evaluated as a bolus drug delivery system and have minimal to no toxic effects (Einmahl, S.; Ponsart, S.; Bejjani, R. A.; D'Hermies, F.; Savoldelli, M; Heller, J.; Tabatabay, C.; Gurny, R.; Behar-Cohen, F. *Ocular biocompatibility of a poly(orthoester) characterized by autocatalyzed degradation. Jthenal of Biomedical Materials Research, Part A,* 2003, 67, 44-53), this polymer has not been used to generate nanoparticles for use as an intraocular delivery system.

To avoid frequent intravitreal injections, which can cause complications such as endophthalmitis and retinal detachment, a biodegradable, biocompatible, and long-term controlled release drug delivery system is highly desirable.

SUMMARY OF THE INVENTION

The object of this invention is to provide a poly(ortho ester) nanoparticle drug delivery carrier to treat various intraocular diseases, such as age-related macular degeneration, retinal detachment, Leber congenital amaurosis and diabetic retinopathy. This nanoparticle drug delivery system has many technological advantages, such as an ability to encapsulate hydrophilic and lipophilic molecules, narrow range size distribution, high encapsulation efficiencies, long term drug delivery with a zero-order kinetics, degradation mediated drug delivery, well controlled surface erosion, and cytocompatibity. More specifically the present invention provides a poly(ortho ester) polymer nanoparticle drug delivery system generated from poly(ortho ester) polymers with sustained zero-order drug release capability.

In one embodiment, a plurality of blank biodegradable poly(ortho ester) nanoparticles having a substantially homogeneous distribution are disclosed. A substantially homogeneous distribution of poly(ortho ester) nanoparticles has a low polydispersity index. The polydispersity index is a measure for the size distribution of the nanoparticles, wherein values between 1 (maximum dispersion) and 0 (identical size of all the particles) are theoretically possible. The low polydispersity index of the nanoparticles according to the invention of at the most 0.25 ensures a selective and controllable transport of the bioactive agent as well as the release of the active substance at the desired target site, in particular, during the absorption of the nanoparticles by body cells. However, nanoparticles compositions with a polydispersity index of between 0.1 and 0.25 are particularly preferred.

In another embodiment, the composition further includes at least one bioactive agent dispersed through-out the nanoparticles, wherein a polydispersity value of the composition is lower than the polydispersity value of the blank poly(ortho ester) nanoparticles.

In another embodiment, the composition of further includes a therapeutically effective amount of at least one bioactive agent, wherein the bioactive agent is dispersed through out the nanoparticles and wherein the nanoparticles are formulated to deliver with zero-order kinetics a bioactive agent.

In a preferred embodiment, a novel formulation of the drug-loaded poly(ortho ester) nanoparticles (NP) with poorly water soluble drugs aimed at improving the ocular bioavailability of the drugs to offer new options in the treatment of chronic eye diseases, such as age-related macular degeneration and diabetic retinopathy is disclosed. In one preferred embodiment, the lipophilic drug is celecoxib. In another preferred embodiment, the encapsulate molecule is a multivalent N-linked glycan.

In a preferred embodiment, poly(ortho ester) nanoparticles are synthesized and characterized by using two synthesis methods to accommodate drugs of varying hydrophilicity and lipophilicity: double emulsion solvent evaporation (DESS); and double emulsion solvent diffusion (DESD). The double emulsion solvent evaporation technique and also double emulsion solvent diffusion technique, an alternative method to load hydrophilic drugs, are water in oil in water [(W/O)/W] methods, which are useful for loading hydrophilic drugs into poly(ortho ester) nanoparticles. The average diameter of a poly(ortho ester) nanoparticles loaded with a hydrophilic bioactive agent prepared by solvent evaporation method ranges from about 241 to 298 nm (0.10-0.25 polydispersity index).

The double emulsion solvent diffusion technique is oil in water in water [(O/W)/W] method that is useful for loading lipophilic drugs into poly(ortho ester) nanoparticles. In this instance, the average diameter of a poly(ortho ester) nanoparticles loaded with a lipophilic bioactive agent ranges from about 151-165 nm (0.08-0.12 polydispersity index).

One embodiment is a method for loading nanoparticles with hydrophilic drugs using double emulsion solvent evaporation. Drug loaded nanoparticles were formulated using a preferred double emulsion solvent evaporation system. The method includes the steps of: (a) hydrophilic drug was dissolved in water, (b) poly(ortho ester) was dissolved in an organic solution, (c) the aqueous drug solution was added to the poly(ortho ester) organic solution and sonicated to form a primary water-in-oil (W/O) emulsion, (d) this W/O emulsion was further added to emulsifying agent to achieve the water-in-oil-in-water [(W/O)/W] double emulsion system, (e) the organic solvents were allowed to evaporate, (f) the solidified nanoparticles were collected and dried.

A related embodiment of the invention is a method for loading nanoparticles with hydrophilic drugs using double emulsion solvent diffusion method. The method includes the steps of: (a) hydrophilic drug was dissolved in water, (b) the hydrophilic drug solution was further emulsified in an organic solution containing poly(ortho ester) polymer and emulsifying agent (c) the resulting primary W/O emulsion was added to water and was sonicated to form the water in oil in water double emulsion. The remaining steps were essentially as described above.

Yet another aspect of the invention is a method for loading nanoparticles with lipophilic drugs using double emulsion solvent diffusion method. The lipophilic drug was preferably encapsulated in poly(ortho ester) nanoparticles by using the double emulsion solvent diffusion method. The method includes the steps of: (a) poly(ortho ester) and lipophilic drug were dissolved in an organic solution, (b) the organic phases were added into an aqueous phase containing emulsifying agent as a stabilizer, (c) then the mixture was emulsified with sonicator, (d) in order to allow for diffusion of the organic solvent into water, a volume of purified water was subsequently added to the 0/W emulsion, leading to the formation of lipophilic drug-loaded poly(ortho ester) nanoparticles. The remaining steps were essentially as described above.

BRIEF DESCRIPTION OF THE DRAWINGS

The following drawings form part of the present specification and are included to further demonstrate certain aspects of the present invention. The invention may be better understood by reference to one or more of these drawings in combination with detailed description of specific embodiments presented herein. The patent or application file contains at least one drawing executed in color. Copies of this patent or patent application publication with color drawing(s) will be provided by the Office upon request and payment of the necessary fee.

FIG. 6 A-E illustrates safety studies of triantennary N-linked oligosaccharide (NA3), an exemplary N-linked oligosaccharide.

FIG. 7 A-E illustrates safety studies of an exemplary nanoparticle.

FIG. 14G illustrates confocal fluorescence microscopy images of Müller cells after exposure to Nile red-loaded poly(ortho ester) nanoparticles before washing and FIG. 14H illustrates confocal fluorescence microscopy images of Müller cells after exposure to Nile red-loaded nanoparticles. Magnification in FIG. 14 A-G is 50 µm and in FIG. 14H is 500 nm. Cell membranes and nuclei were labeled with OREGON GREEN 488 DHPE (Invitrogen; Grand Island, N.Y.) and TO-PRO-3 IODIDE (Invitrogen; Grand Island, N.Y.) and are shown in green and blue, respectively.

DETAILED DESCRIPTION OF THE INVENTION

Figure 1A:
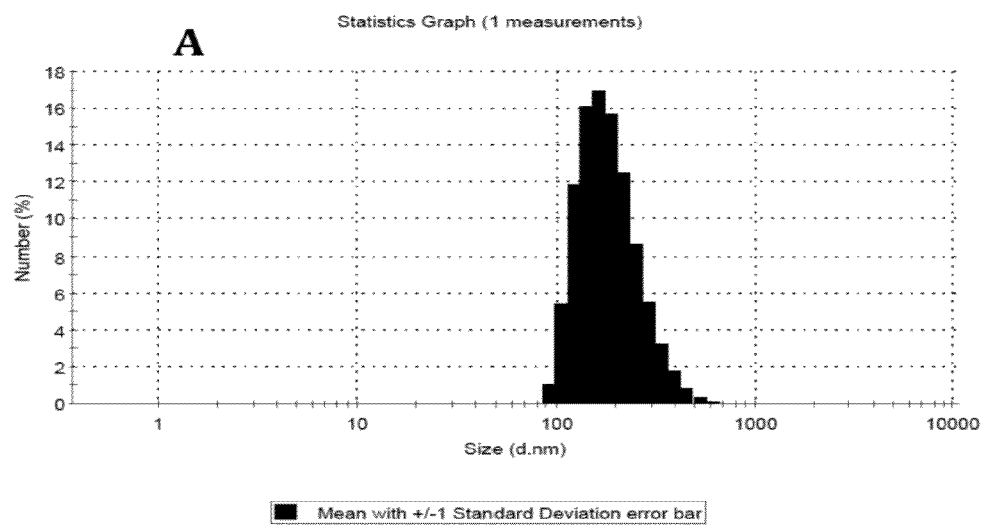
FIG. 1A shows the narrow particle size distribution of 22 kD double emulsion solvent evaporation-nanoparticles.

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

This present invention discloses for the very first time, poly(ortho ester) nanoparticles synthesis and characterization with the goal of designing a drug delivery carrier to treat various intraocular diseases, such as age-related macular degeneration, glaucoma, retinal detachment, Leber congenital amaurosis and diabetic retinopathy. A nanoparticle drug delivery system has many technological advantages such as an ability to encapsulate both hydrophilic and lipophilic molecules, has a narrow range size distribution, high encapsulation efficiencies, offers long term drug delivery with a zero-order kinetics, has degradation-mediated drug delivery, well controlled surface erosion, and cytocompatibity. When poly(ortho ester) nanoparticles injected intravitreally in rabbits and mice, they localized and remained in the vitreous chamber minimum for two weeks without any toxic side effects.

The present invention provides a nanoparticle delivery system made from poly(ortho ester) polymers. A bioactive agent, such as a drug is dispersed through out these nanoparticles. The bioactive agents dispersed through out the poly(ortho ester) nanoparticles, include but are not limited to lipophilic, hydrophilic small and large molecules and also hydrophilic and lipophilic dyes by adopting appropriate emulsion techniques. Additionally, these poly(ortho ester) nanoparticles are biodegradable, biocompatible and provide a controlled release drug delivery system with zero order kinetics, which can be used in various biomedical applications like eye-related diseases, cancer, arthritis, etc.

The present invention provides for dispersion of a bioactive agent, e.g. a drug, through out the plurality of a homogeneous distribution of poly(ortho ester) nanoparticles. It is understood that drug loading percent and encapsulation efficiency percent are calculated by using following formulas:

$$\text{Drug loading \%} = \frac{\text{Total amount of the drug loaded in nanoparticles}}{\text{Weight of nanoparticles}} \times 100$$

$$\text{Encapsulation efficiency } (EE \%) = \frac{\text{Total amount of the drug loaded in nanoparticles}}{\text{Initial amount of the drug taken for loading studies}} \times 100$$

The sustained release delivery system is made of a poly(ortho ester) nanoparticle formulated to linearly deliver a bioactive agent, such as a drug, for at least 14 weeks. Poly(ortho ester) is a lipophilic polymer and has been used in bioerodible drug delivery systems. Poly(ortho ester) can be degraded by surface erosion confined to the polymer—water interface which follows zero-order release kinetics when placed in a biological environment. Additionally, the degradation products of poly(ortho ester) are non-toxic to biomedical systems. See Einmahl, S.; Ponsart, S.; Bejjani, R. A.; D'Hermies, F.; Savoldelli, M.; Heller, J; Tabatabay, C; Gurny, R.; Behar-Cohen, F. *Ocular biocompatibility of a poly(orthoester) characterized by autocatalyzed degradation. Jthenal of Biomedical Materials Research, Part A,* 2003, 67, 44-53; Schwach-Abdellaoui, K.; Loup, P.; Vivien-Castioni, J.; Mombelli, N; Baehni, A.; Barr, P.; Heller, J; Gurny, R.; *Bioerodible Injectable Poly(ortho ester) for Tetracycline Controlled Delivery to Periodontal Pockets: Preliminary Trial in Humans, AAPS pharmaceutical science,* 4, 2002, 1-7).

There are various factors affecting the release of the bioactive agent from the poly(ortho ester) nanoparticle, such as molecular weight and degradation behavior of the poly(ortho ester), degradation further depends on the autocatalysis, glass transition temperatures, lipophilicity nature of the poly(ortho ester). Release of the bioactive agent from the poly(ortho ester) nanoparticle also affected by the amount of bioactive agent encapsulated in the poly(ortho ester) nanoparticles. The molecular weight of the poly(ortho ester) polymer is generally one of the factors affecting the drug release. Molecular weight is indicative of chain length of the polymer and the higher the molecular weight, the longer is the chain length. Furthermore, chain length reflects the hydrophilicity/lipophilicity of the polymer. An increase in chain length increases the lipophilicity and decreases the degradation rate of the polymer. Therefore, by varying the molecular weight, the degradation rate of the polymer and release kinetics of the drug can be controlled accordingly.

Additionally, the erosion rate of a poly(ortho ester) polymer is controlled by the incorporation of a latent acid such as lactic acid (LA), resulting in a $4^{th}$ generation poly(ortho ester) polymer (poly(ortho ester) IV) (Schwach-Abdellaoui, K; Heller, J; Gurny, R. *Hydrolysis and erosion studies of autocatalyzed poly(ortho esters) containing lactoyl-Lactyl acid dimers, Macromolecules* 1999, 32, 301-307). Polymer erosion rate increases, if the concentration of lactic acid increases in the polymer chain. Hence, the erosion rate of poly(ortho ester) is clearly related to the concentration of lactic acid incorporation in the polymer backbone. The drug loaded in nanoparticle delivery systems can be released from the system by diffusion, swelling, erosion, or degradation. (Bala I, Hariharan S, Kumar M N.; *PLGA nanoparticles in drug delivery: the state of the art, Critical Reviews in Therpeutic Drug Carrier Systems,* 21, 2004, 387-422).

It is further understood "degradation" refers to the process that progressively reduce the molecular weight of the macromolecules. "Biodegradable" is understood by a person of the ordinary skill of the art as the capability to break down a pharmaceutical agent naturally by the action of biological agents.

The term "surface erosion" is the process of constant weight loss from the polymer matrix exterior surface. For ideal surface erosion, erosion rate is directly proportional to external surface area. Thus, the erosion rate is essentially constant until the polymer is completely eroded.

In one embodiment of the present invention, using methods described herein, a poly(ortho ester) polymer was synthesized by a condensation reaction between 1,10 decane diol and a diketene acetal such as 3,9-diethylidene-2,4,8,10-tetraoxaspiro[5.5]undecane. Autocatalyzed poly(ortho esters), [poly(ortho ester)$_{95}$LA$_5$ where LA stands for lactic acid and 95 and 5 the molar ratios of ortho ester and lactic acid units], is synthesized by an acid-catalyzed condensation of 3,9-diethylidene-2,4,8,10-tetraoxaspiro[5.5]undecane (DETOSU) with 1,10-decanediol and 1,10-decanediol dilactate (Schwach-Abdellaoui, K.; Heller, J.; Gurny, R. *Hydrolysis and erosion studies of autocatalyzed poly(ortho esters) containing lactoyl-Lactyl acid dimers, Macromolecules* 1999, 32, 301-307). The diketene acetal, DETOSU was prepared from a base-catalyzed rearrangement of the commercially available precursor 3,9-divinyl-2,4,8,10-tetraoxaspiro-[5.5]-undecane (DVTOSU), as described in Ng et al. (Ng, S. Y; Shen, H. R.; Lopez, E.; Zherebin, Y; Barr, J.; Schacht, E.; Heller, J. *Development of a poly(orthoester)prototyoe with a latent acid in the polymer backbone for 5-fluortheacil delivery. J. Control. Release* 2000, 65, 367-374). 1,10-decanediol-lactate was synthesized by a ring opening of lactide (Schwach-Abdellaoui, K.; Heller, J.; Gurny, R. *Hydrolysis and erosion studies of autocatalyzed poly(ortho esters) containing lactoyl-Lactyl acid dimers, Macromolecules* 1999, 32, 301-307).

More specifically, poly(ortho ester)$_{95}$LA$_5$ was synthesized as follows: 796 mg of 1,10-decanediol-lactate ($2.5\times10^{-3}$) and 8.277 g of 1,10-decanediol ($47.5\times10^{-3}$) are dissolved in 60 ml of anhydrous tetrahydrofuran (THF). The solution was stirred and gently heated until complete dissolution of the monomers took place. Then, 10.613 g of DETOSU ($50\times10^{-3}$) is added under argon atmosphere and the polymerization initiated by the addition of p-toluene sulphonic acid w/w 1% solution in anhydrous tetrahydrofuran. The exothermic reaction produces polymer almost instantaneously. The stirring is maintained for 1 hr at room temperature and the polymer then precipitated with methanol containing five drops of triethyleneamine (TEA) to stabilize the polymer. Low molecular weight oligomers, unreacted monomers, and catalyst are removed by a dissolution-precipitation method with tetrahydrofuran and methanol as solvent and non-solvent, respectively. The precipitated polymer was dried under vacuum at 40° C. for 48 h. and stored in a desiccator.

The term "encapsulation" used herein refers to the amount of pharmaceutical agent incorporated into the nanoparticle carrier. In the present invention, poly(ortho ester) nanoparticles were able to encapsulate a variety of hydrophilic and lipophilic molecules by adopting appropriate emulsion method, such as, epinephrine, vancomycin hydrochloride, rhodamine 6G, celecoxib, Nile red etc. Further, in one embodiment of the present invention, poly(ortho ester) nanoparticles are synthesized and characterized by the following procedures. The poly(ortho ester) nanoparticles are prepared using two synthesis methods to accommodate drugs of varying hydrophilicity and lipophilicity: double emulsion solvent evaporation and double emulsion solvent diffusion, respectively.

Double emulsion solvent evaporation technique is a water in oil in water [(W/O)/W] method which is useful for loading hydrophilic drugs into poly(ortho ester) nanoparticles. To do so, the hydrophilic drug is dissolved in water and combined with poly(ortho ester) that is dissolved in solvent. Both of these phases are mixed and emulsified by using sonicator probe to form a W/O emulsion. Because the water phase forms the core of the nanoparticle, a hydrophilic drug dissolved in water will be encapsulated by the nanoparticles (double emulsion solvent evaporation-nanoparticles) as they are solidified. Hydrophilic drugs include water-soluble molecules, such as epinephrine, rhodamine 6G and bovine serum albumin (BSA).

The double emulsion solvent diffusion technique is oil in water in water [(O/W)/W] method that is useful for loading lipophilic drugs into poly(ortho ester) nanoparticles. To do so, the lipophilic drug and poly(ortho ester) are dissolved in solvent, which is then saturated with the water phase and emulsified using a sonicator probe to form an O/W emulsion. Because the solvent phase forms the core of the nanoparticle, the lipophilic drug dissolved in solvent will be encapsulated by the nanoparticles (double emulsion solvent diffusion-nanoparticles) as it is solidified. Examples of lipophilic drugs include: water-insoluble molecules such as celecoxib, Nile red, triamcinolone acetonide and budesonide.

The present invention provides that the poly(ortho ester) nanoparticles, prepared by solvent evaporation to load hydrophilic drugs and solvent diffusion method to load lipophilic drugs, have showed mean particles diameter of 241-298 nm and 151-164 nm, respectively.

The invention relates to compositions made of nanoparticle-based drug delivery system thereof that are capable of treatment of subjects with intraocular diseases. In some embodiments, the subject of treatment is a human. In other embodiments, the subject is a veterinary subject. Treatment may involve administration of one or more, therapeutic agent that are encapsulated by poly(ortho ester) nanoparticle carrier.

The compositions of the invention may include a "therapeutically effective amount" or a "prophylactically effective amount" of pharmaceutical portion of the invention. A "therapeutically effective amount" refers to an amount effective, at dosages and for periods of time necessary, to achieve the desired therapeutic result. A therapeutically effective amount of the pharmaceutical portion may vary according to factors such as the disease state, age, sex, and weight of the subject, and the ability of the antibody or antibody portion to elicit a desired response in the subject. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

In another embodiment polymeric nanoparticles specifically poly(ortho ester) nanoparticles as described herein are used as carriers for drug delivery to the posterior segment of the eye. The release of poly(ortho ester) nanoparticles may be sustained or controlled by addition of latent acids.

The composition of present invention may also be formulated in a compatible pharmaceutically acceptable carrier, which may also be prepared, placed in an appropriate container, and labeled for treatment of an indicated condition.

A pharmaceutically acceptable carrier is used to deliver the nanoparticles. A pharmaceutically acceptable carrier can be sterile phosphate buffer saline, balanced salt solution, etc.

As used herein the term "intraocular disease" refers to any disease affecting cells in the inside of the eye. Examples of such are age-related macular degeneration, glaucoma, diabetic retinopathy, Leber congenital amaurosis, and retinal detachment. In further embodiment of the present invention, the nanoparticle delivery system is used to place a drug specifically where it is needed, namely deep within the layers that line the interior surface of the eye. While the focus of this preferred embodiment is delivery of drugs to the retina a closed system into which delivery of drugs is limited, it is believed that the nanoparticles of the present invention can be used to deliver drugs to other tissues within the body for the treatment of a wide variety of diseases and disorders, including but not limited to Anti-VEGF therapies (Avastin, Lucentis, Macugen, Eylea) which requires monthly intravitreal injection of anti-VEGF antibodies or fragments; AREDS2—daily oral supplementation of high doses of macular xanthophylls (lutein and zeaxanthin) and omega-3 long-chain polyunsaturated fatty acids; Fenretinide—daily oral supplementation of synthetic analog of retinoic acid which causes a reduction of A2E levels; OT-551-3x/day eye drops which down regulates the overexpression of nuclear factor kappa-light-chain-enhancer of activated B cells (NF-kB), a transcription factor that is highly activated in times of oxidative stress, inflammation, and angiogenesis; Copaxone—weekly subcutaneous injection of an immunomodulatory substance; Sirolinus—daily subcutaneous injection of an immunosuppressant drug; CNTF—intraviteal implant, encapsulated cell technology which slows photoreceptor degeneration in animal models of hereditary retinal disease and thus it is hypothesized that it may be protective in age related macular degeneration. Implant must be surgically removed when spent; Brimonidine—intravitreal implant containing an alpha2-adrenergic agonist that has been used to lower intraocular pressure and has putative neuroprotective properties; and Celecoxib—oral supplementation for patients undergoing photodynamic therapy to stop new blood vessel growth in Age-related Macular Degeneration (AMD) patients. Only ciliary neutrotrophic factor (CNTF), Brimonidine and anti-vascular endothelial growth factor (anti-VEGF) treatments are currently being evaluated as intraocular therapies; all others are systemically administered.

In vitro drug release profiles of epinephrine and celecoxib were evaluated as examples of hydrophilic and lipophilic drugs, respectively. The double emulsion solvent evaporation method was used to load epinephrine, a hydrophilic drug, whereas the double emulsion solvent diffusion method was used to load celecoxib, a lipophilic drug. Nanoparticles prepared using both methods released the drugs with zero-order kinetics. This means that the drug was released at a rate that is independent of time and that the concentration of drug released is within a pharmaceutical dosage range. The cumulative release of drug plotted vs. time indicated a linear relationship between the parameters. Very high correlation coefficients were calculated for all types of nanoparticles that were evaluated Importantly, a burst release was not observed from nanoparticles generated using either method and unlike published studies using bolus poly(ortho ester) polymer, poly (ortho ester) nanoparticles did not show initial lag time prior to drug release.

In vitro drug release studies reveals that, drugs are released from poly(ortho ester) nanoparticles for at least 14 weeks with zero-order kinetics. Drug release from these nanoparticles is mediated by polymer degradation. Poly(ortho ester) nanoparticles show controlled surface erosion, which is explained by measuring one of the degradation products of the polymer for a minimum of 14 weeks.

During a period of 14 weeks, 0.875 mg (20.45%) and 0.854 mg (13.50%) of epinephrine released into phosphate buffered saline from double emulsion solvent evaporation-nanoparticles made from the 22 kD and 5 kD polymers, respectively. In comparison, 0.302 mg (1.53%) and 0.29 mg (1.53%) of celecoxib was released into phosphate buffered saline from double emulsion solvent diffusion-nanoparticles made from the 22 kD and 5 kD polymers, respectively. Given the zero-order release of drug and the rate at which it is being released, a single injection of epinephrine loaded nanoparticles made from 22 kD and 5 kD poly(ortho ester) is expected to provide long-term delivery for 70 and 107 weeks, respectively. Likewise, it is expected that celecoxib will continue to be released for ~900 weeks from nanoparticles made from both 22 and 5 kD polymer.

In the present invention, poly(ortho ester) nanoparticles are not toxic towards cell lines and also not internalized by cells. This property is very important to treat chronic intraocular diseases to maintain long-term drug availability at the site of action. The present invention discloses Intravitreally injected poly(ortho ester) nanoparticles into mouse eyes, show the residence time for at least 3 days without movement into retinal tissues. Further, intravitreal injections of poly(ortho ester) nanoparticles do not cause any toxic side effects to the rabbit eyes and are very well localized in the rabbit vitreous for at least 2 weeks of time.

Figure 2A:
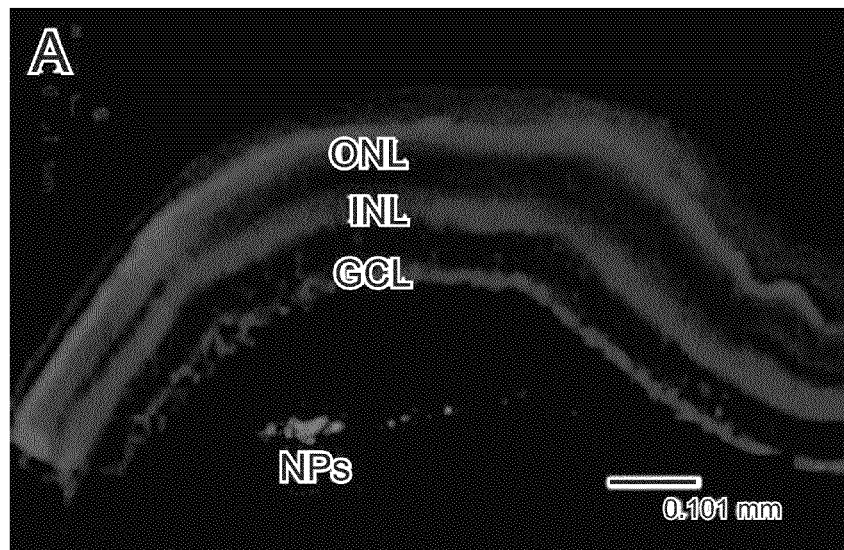
FIG. 2 shows photographs of confocal fluorescence microscopy images of sections taken through eyes after injection of Nile red-loaded nanoparticles. At both 3 hours (A) and 24 hours (B) after injection, the nanoparticles remain in the vitreal chamber of the eye. ONL=outer nuclear layer (photoreceptor nuclei); INL=inner nuclear layer (interneuron nuclei); and GCL=ganglion cell layer. Blue indicates nuclei and red indicates nanoparticles.
Figure 2B:
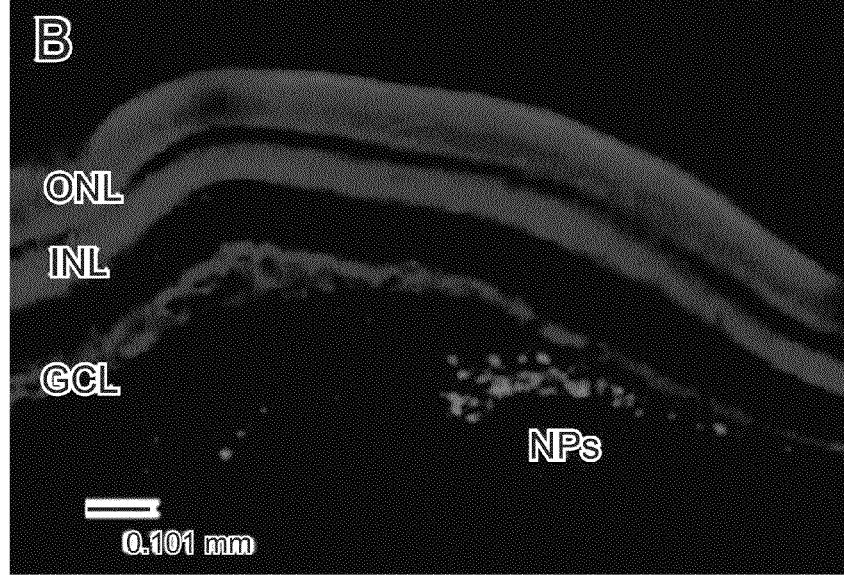

Now referring to FIG. 2, Nile red-loaded nanoparticles were injected into the vitreal chamber of the eye of C57BL/6J mice. Their movement is imaged using standard confocal microscopy. The purpose of these studies is to determine if the nanoparticles remain in the vitreous or if they migrate into the retina. Ideally, the nanoparticles should remain in the vitreous where they would continue to release triantennary N-linked oligosaccharide, a novel drug, for long-term delivery. These results demonstrate that the nanoparticles remain in the vitreous for up to 24 hthes and that none enter the retina. Accordingly, these results demonstrate that biodegradable, biocompatible, and long term controlled release poly(ortho ester) nanoparticles can serve as an ideal drug delivery carrier to deliver drugs to posterior segment of the eye.

To optimize the sonication speed, three kinds of emulsions were prepared by using 45%, 55%, and 65% power intensity. Among these emulsions, nanoparticles prepared from 65% power intensity gave a small size distribution. Sonication time was also optimized, by sonicating the emulsions for various time points, such as, 90 sec, 180 sec and 360 sec. poly(ortho ester) nanoparticle emulsions sonicated for 90 sec, gave smaller size distribution than rest of the emulsions. Hence, 65% power intensity and 90 sec of sonication time were optimal factors of speed and time to prepare poly(ortho ester) nanoparticles by double emulsion solvent diffusion-hydrophilic method.

Figure 3A:
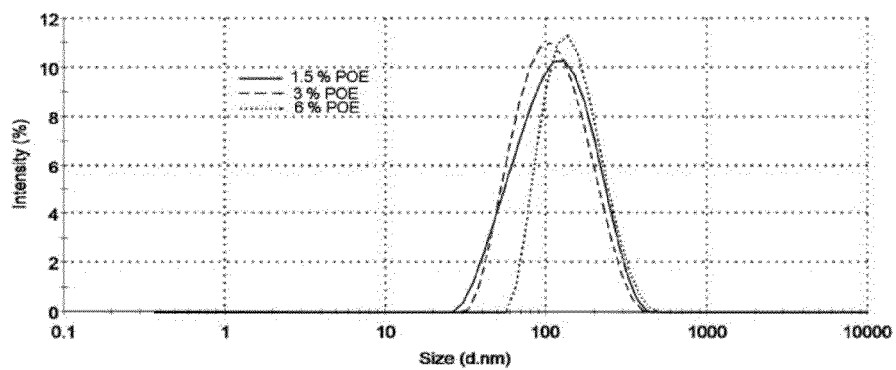
FIG. 3A is the effect of various polymer concentrations on the particle size distributions of the poly(ortho ester) nanoparticles prepared by double emulsion solvent diffusion-hydrophilic method, when PLURONIC F-68 (Sigma Aldrich; St. Louis, Mo.) was used as a surfactant.

Now referring to FIG. 3A, the effect of polymer concentration on particle size is shown. Stable and transparent emulsions were formed by increasing poly(ortho ester) concentration from 1.5% to 6%, when solvent ethyl acetate, stabilizer used for the preparation of nanoparticles. Particle size distributions were ranged from 96 to 129 nm and slight change was seen with the polymer concentration. Based on the results, 3% of polymer concentration was chosen to further optimize the emulsification parameters.

Figure 3B:
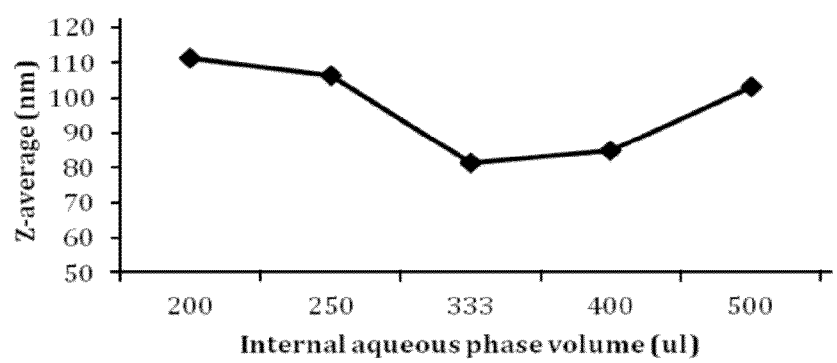
FIG. 3B shows the optimization of internal aqueous phase volume in double emulsion solvent diffusion-hydrophilic method, when ethyl acetate and PLURONIC F-68 (Sigma Aldrich; St. Louis, Mo.) used as organic solvent and surfactant.

The volume of internal aqueous phase is optimized to generate narrow range size distribution of poly(ortho ester) nanoparticles by keeping the other parameters like solvent ethyl acetate (EA), concentration of poly(ortho ester) (3%) and PLURONIC F-68 (Sigma Aldrich; St. Louis, Mo.) (3%) constant. Various emulsions were prepared by using 100 to 500 μL of internal aqueous phase. Particles were not formed with 100 and 150 μL of aqueous phase. Now referring to FIG. 3B, shows the particle size changes based on the aqueous phase volume used. Nanoparticles emulsions made with 333 μL of internal aqueous phase measured smallest mean size distribution in comparison with rest of the emulsions.

TABLE 1

Solubility of various organic phase solvents in water or Poly(ortho ester) polymer.

| | Ethyl acetate | Dichloromethane | Acetone | MEK | Chloroform |
|---|---|---|---|---|---|
| Water | Slightly soluble (8.7% (w/w) at 25° C.) | Immiscible (1.6% (w/w) at 25° C.) | Very soluble (infinitely at 25° C.) | Slightly soluble (24% (w/w) at 25° C.) | Immiscible (0.8% w/w at 25° C.) |
| POE | Good solvent | Excellent solvent | Immiscible | Good solvent | Excellent solvent |

In the formation of poly(ortho ester) nanoparticles by the double evaporation solvent diffusion (DESD) technique, both the organic solvent phase containing poly(ortho ester) and aqueous phase containing stabilizer are in the state of thermodynamic equilibrium. The addition of water to the system destabilizes the equilibrium. It causes the organic solvent to diffuse to the external phase. During this transport of the solvent, poly(ortho ester) nanoparticles are produced, and their size may be dependent upon the type of organic phase solvents.

Figure 3C:
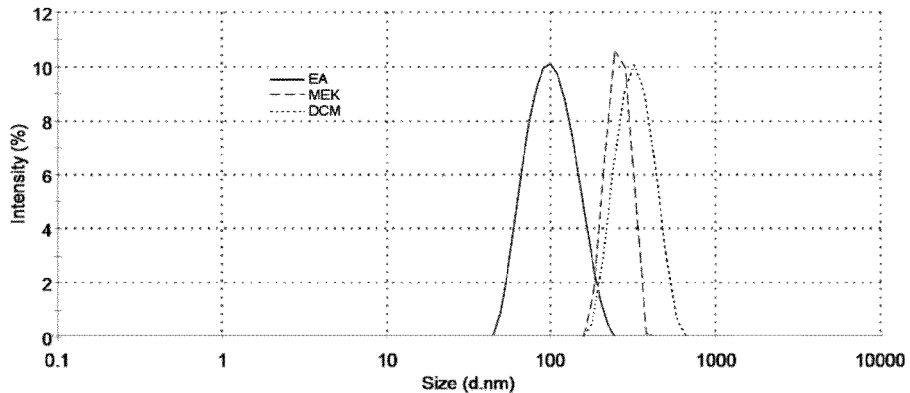
FIG. 3C illustrates the effect of different organic phase solvents on the particle size distribution of the poly(ortho ester) nanoparticles, when PLURONIC F-68 (Sigma Aldrich; St. Louis, Mo.) used as a stabilizer.

Now referring to FIG. 3C, the effect of the type of organic phase solvents on the mean particle size of poly(ortho ester) nanoparticles was evaluated. To evaluate the effect of organic phase solvents, various organic solvents were used for the preparation of poly(ortho ester) nanoparticles.

Table 1 shows a summary of the solubility of the organic phase solvents used for nanoparticle preparation in water or that of the poly(ortho ester) in organic phase solvents. Ethyl acetate and methyl ethyl ketone are partially water-soluble and are good solvents for poly(ortho ester). Acetone is completely miscible with water in all proportions and is a non-solvent for highly hydrophobic poly(ortho ester). Dichloromethane is immiscible with water and is an excellent solvent for poly(ortho ester).

The particle size distributions of the poly(ortho ester) nanoparticles prepared with different organic phase solvents, when PLURONIC F-68 (Sigma Aldrich; St. Louis, Mo.) as a stabilizer is used at a constant concentration of 3% (w/v) with respect to the amount of solvent were studied to optimize the choice of solvent. Small particles below 96 nm in mean particle size were obtained using partially water-soluble solvents (ethyl acetate), while large particles above 280 nm in mean particle size were obtained using water-immiscible solvent (dichloromethane) and partially miscible solvent (methyl ethyl ketone). Also, the solutions of poly(ortho ester) nanoparticles obtained from ethyl acetate as an organic phase solvents were more transparent optically than those of dichloromethane and methyl ethyl ketone. This means that the type of organic phase solvents plays an important role in the mean size of nanoparticles when using PLURONIC F-68 (Sigma Aldrich; St. Louis, Mo.) as a stabilizer. Since nanoparticles are formed from the emulsion droplets after organic solvent diffusion, their size is dependent on the stability of the emulsion droplets, which collide and coalesce among themselves. When the stabilizer remains at the liquid-liquid interface during the diffusion process, and its protective effect is adequate, nanoparticles will form. Small particle sizes for ethyl acetate were attributed to both the adequacy of the stabilizer's protection against coalescence, and the low interfacial tension between aqueous and organic phases, resulting from their partially water-soluble nature. However, when dichloromethane was used as the organic phase solvent, nearly every formulation resulted in significant aggregation due to its immiscible nature with water, and the stabilizer PLURONIC F-68 (Sigma Aldrich; St. Louis, Mo.) is not able to completely prevent aggregation of emulsion droplets, leading to large mean particle size (334 nm). On the other hand, as methyl ethyl ketone has 24% solubility in water, which is greater than ethyl acetate solubility (8.7%) in water, particles smaller than 96 nm are expected. In contrast, particle size measured by using methyl ethyl ketone solvent is 280 nm, which greater than the size of particles obtained by ethyl acetate, which is explained on the basis of solvent-polymer interaction parameter. It could be assumed that when the affinity between the solvent and the polymer was higher, the larger regional super saturation spot was produced. Therefore, the large nanoparticles were formed with methyl ethyl ketone in spite of the higher solvent diffusion capacity than ethyl acetate.

Figure 3D:
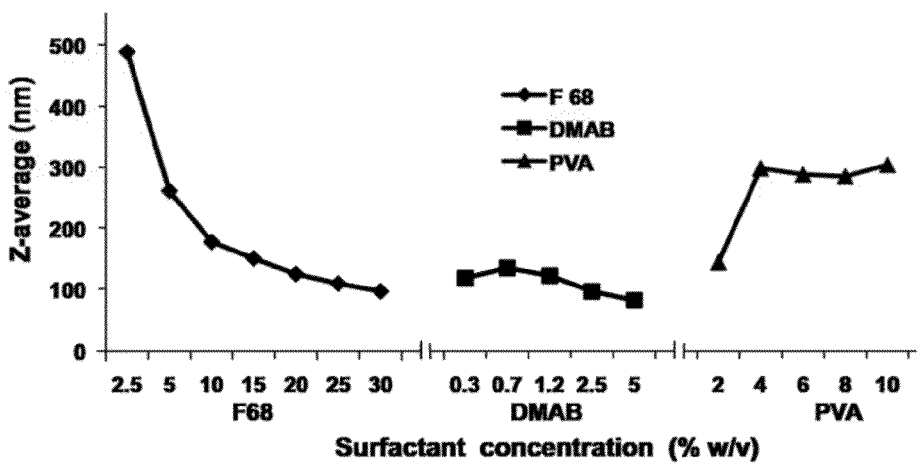
FIG. 3D illustrates the effect of surfactant type and concentration on mean size of poly(ortho ester) nanoparticles prepared by double emulsion solvent diffusion-hydrophilic, when ethyl acetate used as a solvent.

Now referring to FIG. 3D shows the effect of the type and concentration of surfactants on the mean particle size of poly (ortho ester) nanoparticles with ethyl acetate as an organic phase solvent, when PLURONIC F-68 (Sigma Aldrich; St. Louis, Mo.), poly(vinylalcohol), didodecyldimethylammonium bromide (DMAB) and sodium dodecyl sulfate (SDS) are used as stabilizers. Surfactants, PLURONIC F-68 (Sigma Aldrich; St. Louis, Mo.), and poly(vinylalcohol) are non-ionic in nature where as didodecyldimethylammonium bromide (DMAB) and sodium dodecyl sulfate (SDS) stabilizers are cationic and anionic in nature respectively. The mean particle sizes for poly(vinylalcohol) and PLURONIC F-68 (Sigma Aldrich; St. Louis, Mo.) were found to decrease sharply, but little change is observed for didodecyldimethylammonium bromide (DMAB) with the change in stabilizer concentration. In non-ionic stabilizer systems poly(vinyl alcohol) and PLURONIC F-68 (Sigma Aldrich; St. Louis, Mo.) particles are stabilized by steric hindrance, but in an ionic stabilizer system didodecyldimethylammonium bromide (DMAB), particles are stabilized by electrostatic repulsion. This indicates that with increasing stabilizer concentration for PLURONIC F-68 (Sigma Aldrich; St. Louis, Mo.) more stabilizer molecules are adsorbed on the interfaces of emulsion droplets, providing increased protection against coalescence and resulting in smaller emulsion droplets. However, for didodecyldimethylammonium bromide, only a small quantity of stabilizer is adsorbed at the interface of emulsion droplets. The excess remains in the continuous aqueous phase and does not play any significant role in the emulsification (Song, K. C.; Lee, H. S.; Choung, I. Y.; Cho, K. I.; Ahn, Y.; Choi, E. J; *The effect of type of organic phase solvents on the particle sire of poly(D,L-Lactide-co-glycolide) nanoparticles, Colloids and surfaces A: Physiochemical Engineering Aspects,* 276, 2006, 162-167). The mean size of poly(ortho ester) nanoparticles prepared using didodecyldimethylammonium bromide, as a stabilizer is smaller than those of poly(vinyl alcohol) and PLURONIC F-68 (Sigma Aldrich; St. Louis, Mo.) whereas microparticles formed using sodium dodecyl sulfate (SDS) as a stabilizer. The mean size of particles was measured as 81 nm for a concentration of 1.5% w/v of didodecyldimethylammonium bromide. The mean nanoparticle sizes were 143 nm and 96 nm when poly(vinyl alcohol) (0.6% w/v) and PLURONIC F-68 (Sigma Aldrich; St. Louis, Mo.) (3% w/v) used respectively.

Optimized nanoparticle emulsions stabilized with PLURONIC F-68 (Sigma Aldrich; St. Louis, Mo.) and didodecyldimethylammonium bromide (DMAB) as surfactants were used for entrapping vancomycin hydrochloride as a hydrophilic drug. Parameters optimized on the basis of small mean size of nanoparticles, were further narrowed down in terms of high yields of encapsulation of vancomycin in poly (ortho ester) nanoparticles. Those parameters were sonication speed, inner aqueous phase (200-333 µl), and concentration and type of stabilizers, PLURONIC F-68 (Sigma Aldrich; St. Louis, Mo.) and didodecyldimethylammonium bromide (DMAB)

Figure 3E:
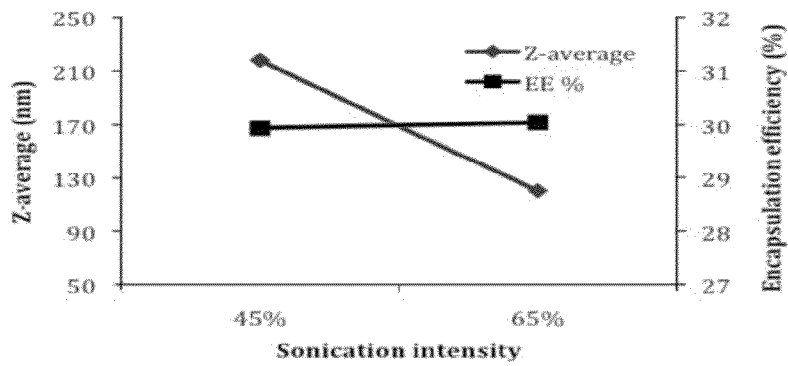
FIG. 3E shows the effect of sonication speed on encapsulation efficiency and particle size of vancomycin-loaded poly(ortho ester) nanoparticles prepared by double emulsion solvent diffusion-hydrophilic method.

Now referring to FIG. 3E, encapsulation efficiencies and average diameters of poly(ortho ester) nanoparticles prepared at two different sonication intensities such as, 45 and 65% are shown. By increasing sonication intensity from 45 to 65%, particle size was decreased from 218 to 120 nm, whereas, encapsulation efficiencies (~30%) were unaffected.

Figure 3F:
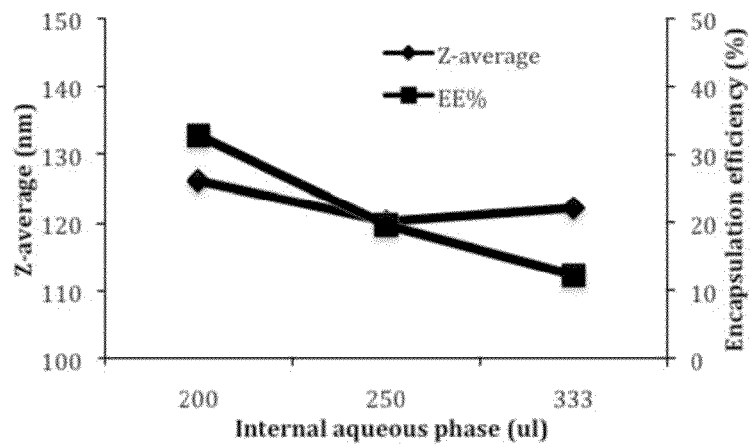
FIG. 3F illustrates the effect of internal aqueous phase volume on encapsulation efficiency and particle size distribution of poly(ortho ester) nanoparticle prepared by double emulsion solvent diffusion-hydrophilic method.

Now referring to FIG. 3F, the encapsulation efficiency and the average particle size of vancomycin-loaded poly(ortho ester) nanoparticle emulsions prepared by varying internal aqueous phase volume (200-333 μL) is shown in with the increase in the volume of internal aqueous phase, a decrease in encapsulation efficiency was observed. Vancomycin-loaded nanoparticle emulsion prepared with 200 μL of internal aqueous phase showed 32.86% EE where as with 250 and 333 μL volume showed 19.71 and 12.3 respectively. Hence, by emulsifying 200 μL of internal aqueous phase containing vancomycin, with 1000 μL of ethyl acetate as an organic solvent and PLURONIC F-68 (Sigma Aldrich; St. Louis, Mo.) as a surfactant at 65% sonication intensity, produce small poly(ortho ester) nanoparticles with high encapsulation efficiency.

Figure 3G:
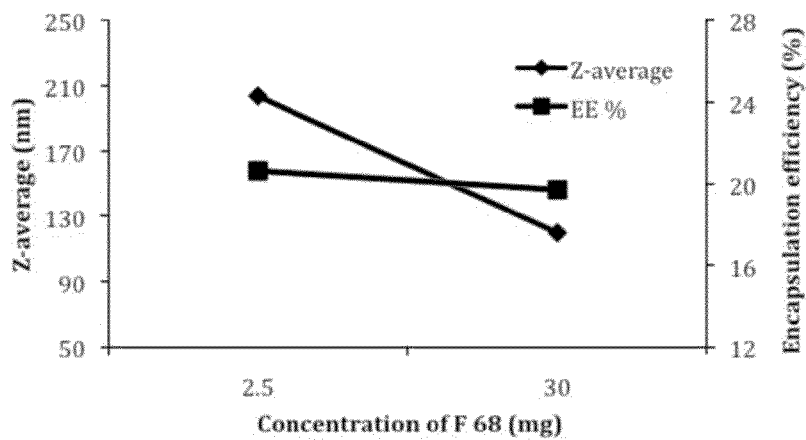
FIG. 3G: The effect of surfactant PLURONIC F-68 (Sigma Aldrich; St. Louis, Mo.) concentration on encapsulation efficiency and mean size of nanoparticles prepared by double emulsion solvent diffusion-hydrophilic method.

Now referring to FIG. 3G, an average size and encapsulation efficiencies of the nanoparticles prepared by using two different concentrations of PLURONIC F-68 (Sigma Aldrich; St. Louis, Mo.) such as, 2.5 mg and 30 mg is shown. Concentration of surfactant PLURONIC F-68 (Sigma Aldrich; St. Louis, Mo.) did not show any influence on the encapsulation efficiency. Blank nanoparticle emulsions prepared with surfactants PLURONIC F-68 (Sigma Aldrich; St. Louis, Mo.) and didodecyldimethylammonium bromide (DMAB) produced smaller particles size (≥100 nm). Based on these results, these two surfactants were selected for vancomycin loading example. Though, emulsions prepared by using didodecyldimethylammonium bromide (DMAB) surfactant measured smaller in particle diameters as compared to PLURONIC F-68 (Sigma Aldrich; St. Louis, Mo.), lesser yield of nanoparticles was observed. Hence, PLURONIC F-68 (Sigma Aldrich; St. Louis, Mo.) is the ideal surfactant, which can provide narrow range distribution, stability and high yield.

Figure 3H:
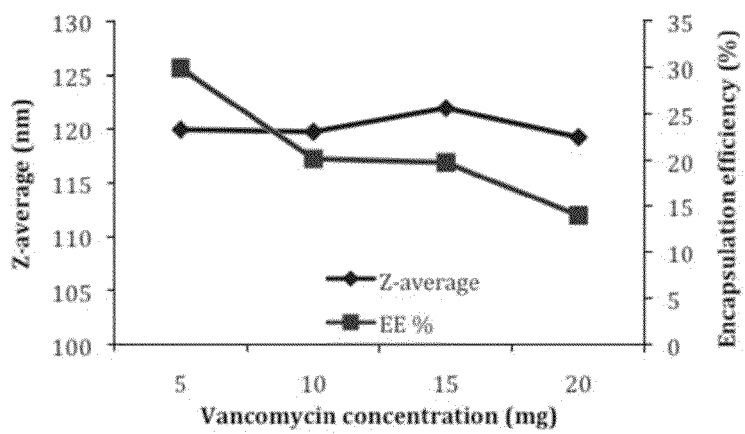
FIG. 3H illustrates the effect of vancomycin concentration on the encapsulation and particles mean size distribution prepared by double emulsion solvent diffusion-hydrophilic method, when 200 µL of inner aqueous phase, and PLURONIC F-68 (Sigma Aldrich; St. Louis, Mo.) as a surfactant at 65% sonication intensity.

Now referring to FIG. 3H, the effect of the proportional amount of drug on the entrapment efficiency was studied by varying the amount of vancomycin (as compared with the amount of the polymer (30 mg) between 5 mg and 20 mg is shown. Here the drug encapsulation efficiency of the particles decreased as the relative amount of the drug substance was increased.

Poly(ortho ester) nanoparticles were prepared using a water-in-oil-in-water [(W/O)/W] double emulsion solvent evaporation (DESE) technique (Palamoor, M and M. M. Jablonski, Poly(ortho ester) Nanoparticle-Based Targeted Intraocular Therapy for Controlled Release of Hydrophilic Molecules. Molecular pharmaceutics, 2013.). Poly(ortho ester) nanoparticle emulsions at various sonication intensities and time points were prepared to optimize sonication speed and time. Table 2 shows the average particle distributions and various process conditions. By increasing the sonication speed from 45%-65%, particle size decreased from 607 nm to 246 nm. But increase in time did not show any effect to achieve small particles size. Hence, 65% of sonication intensity and 90 S of sonication time to prepare poly(ortho ester) nanoparticle emulsions were selected for further optimization procedure.

TABLE 2

Average particle distributions

| Sonication Speed | Sonication time | Z-average | Polydispersity Index |
|---|---|---|---|
| 65% | 90 S | 246.8 | 0.18 |
| 65% | 180 S | 280 | 0.23 |
| 65% | 300 S | 503.4 | 0.253 |
| 45% | 90 S | 607.5 | 0.43 |
| 55% | 90 S | 433 | 0.249 |
| 65% | 90 S | 246.8 | 0.18 |

Figure 4A:
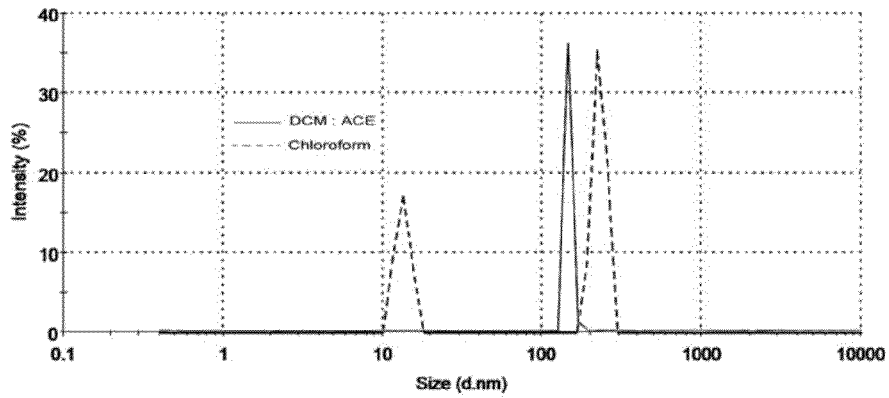
FIG. 4A is the effect of solvent type on mean particle size prepared by double emulsion solvent evaporation, when poly (vinyl alcohol) used in external aqueous phase at 65% sonication intensity for 90 sec.
Figure 4B:
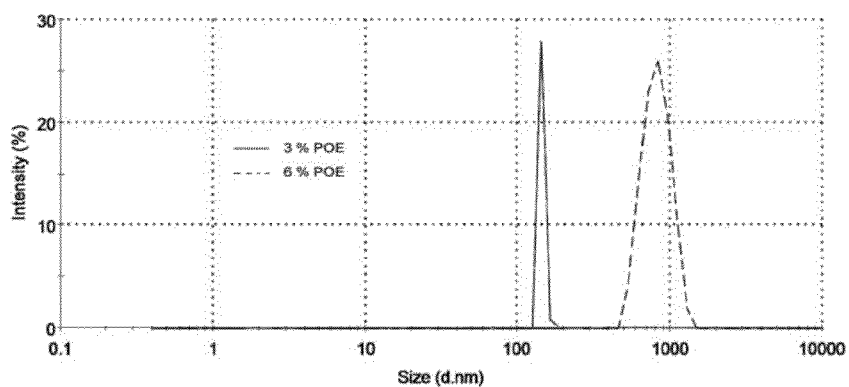
FIG. 4B shows the effect of polymer concentration on nanoparticles size distribution in double emulsion solvent evaporation method, when dichloromethane: acetone and poly (vinyl alcohol) used as solvent mixture and stabilizer in external aqueous phase respectively.

Table 2: Effect of sonication time and speed on nanoparticles mean size prepared by double emulsion solvent evaporation (DESE) method, when Dichloromethane:Acetone (8:2), 0.05% PLURONIC F-68 (Sigma Aldrich; St. Louis, Mo.) and poly(vinyl alcohol) used as a mixture of organic solvent phase, internal and external aqueous phase surfactants respectively. Now referring to FIG. 4A-4B, emulsion prepared with chloroform solvent, produced bigger average particle size than Dichloromethane: Acetone mixture. Polymer concentrations of 1.5, 3 and 6% were screened to choose the appropriate amount of poly(ortho ester) polymer. Nanoparticle emulsion did not formed with 1.5% polymer due to inadequate viscosity of the organic phase. Nanoparticle with 3% and 6% of poly(ortho ester) concentration showed the average particle sizes of 246 and 919 nm.

Figure 4C:
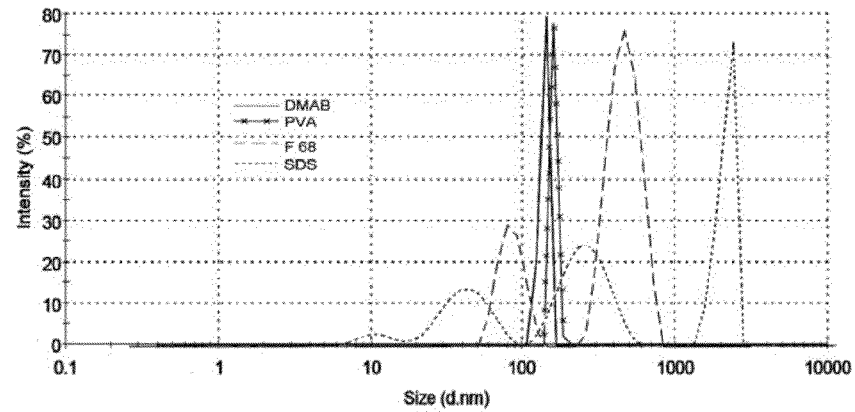
FIG. 4C shows the effect of various stabilizers in external aqueous phase on particle size distribution in double emulsion solvent evaporation method.

Now referring to FIG. 4C, the particles size distribution of emulsion prepared with numerous concentrations of PLURONIC F-68 (Sigma Aldrich; St. Louis, Mo.), such as 0.05 to 0.15% was shown. In this double emulsion solvent evaporation (DESS) method surfactants were used in both inner organic and outer aqueous phase. PLURONIC F-68 (Sigma Aldrich; St. Louis, Mo.) was used in inner organic phase and its optimal concentration was selected based on the narrow range size distribution. It is evidenced from the FIG. 4C, that emulsion made with 0.05% PLURONIC F-68 (Sigma Aldrich; St. Louis, Mo.) had small particle size. A variety of surfactants such as, poly(vinyl alcohol), PLURONIC F-68 (Sigma Aldrich; St. Louis, Mo.), didodecyldimethylammonium bromide (DMAB) and sodium dodecyl sulfate (SDS) were used in outer aqueous phase to achieve narrow range size distributions of poly(ortho ester) nanoparticles. Nanoparticle emulsions prepared with poly(vinyl alcohol) and didodecyldimethylammonium bromide (DMAB) surfactants measured narrow range size distributions.

TABLE 3

Quantification of Nile red in Muller cell uptake studies

| Sample | Time point | Wash I[a] | Wash II[a] | Wash III | Cells |
|---|---|---|---|---|---|
| 1 mg/ml | 2 h | 93.7 ± 0.14 | 3.1 ± 0.002 | n/d | n/d |
| 0.2 mg/ml | 2 h | 94.5 ± 0.054 | 0.56 ± 0.032 | n/d | n/d |
| 1 mg/ml | 24 h | 96.25 ± 0.16 | 0.73 ± 0.003 | n/d | n/d |
| 0.2 mg/ml | 24 h | 95.28 ± 0.05 | n/d | n/d | n/d |

[a]Mean ± standard error (n = 3).
n/d denotes not in a detectable range.

TABLE 4

Quantification of Nile red in HEK 293 cell uptake studies.

| Sample | Time point | Wash I[a] | Wash II[a] | Wash III | Cells |
|---|---|---|---|---|---|
| 1 mg/ml | 2 h | 95 ± 0.22 | 2.4 ± 0.031 | n/d | n/d |
| 0.2 mg/ml | 2 h | 96.2 ± 0.13 | n/d | n/d | n/d |
| 1 mg/ml | 24 h | 97.4 ± 0.06 | 1.8 ± 0.04 | n/d | n/d |
| 0.2 mg/ml | 24 h | 96.7 ± 013 | 0.12 ± 0.11 | n/d | n/d |

[a]Mean ± standard error (n = 3);
n/d denotes not in a detectable range.

To further confirm the Nile red-loaded nanoparticles cell uptake data obtained from confocal images, Nile red was quantified in both Müller and HEK 293 cell lines under various experimental conditions. Tables 3 and 4 show the percentage of Nile red measured in all three washings and cell lysates of both Müller and HEK 293 cells, respectively, In all cases, most of the Nile red was observed in wash I and small quantities were presented in wash II. Nile red in wash III and cell lysates was not in the detectable range. The quantitative data strongly supports the qualitative data, confirming that, poly(ortho ester) nanoparticles were not internalized irrespective of their concentration, cell lines and incubation time.

The retinal glycan binding receptor is shown to play an important role in promoting assembly of outer segment (OS) membranes by the photoreceptor cells of the eye, a process that is essential for vision. Based on the finding that certain sugars can bind with very high affinity to the retinal glycan receptor and stimulate its function, the invention provides novel therapeutic agents for treatment of retinal diseases that are multivalent N-linked glycans. Preferred pharmaceutical compositions in accordance with the present invention comprise active agents having the general formula: (Gal-GlcNAc)$_n$-Man$_3$-GlcNAc2, where n is 1-4. Particularly preferred multivalent glycans are galactosylated, biantennary (NA2), and asialo, galactosylated, triantennary (NA3) oligosaccharides.

Figure 5:
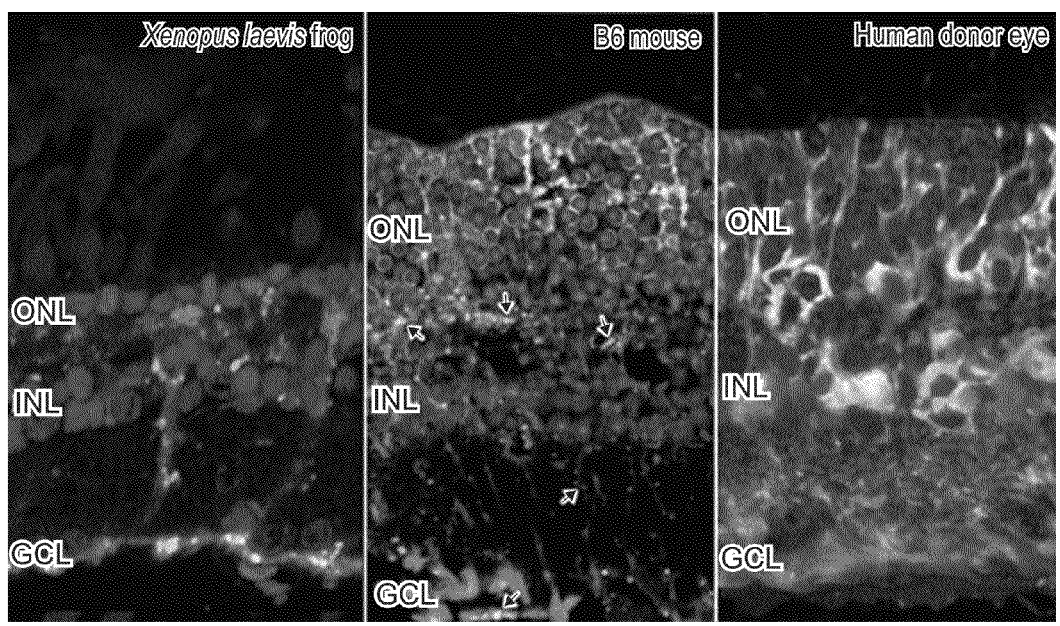
FIG. 5 shows photographs of glycans binding to Muller cell in frog, mouse and human donor eyes.
Figure 6A:
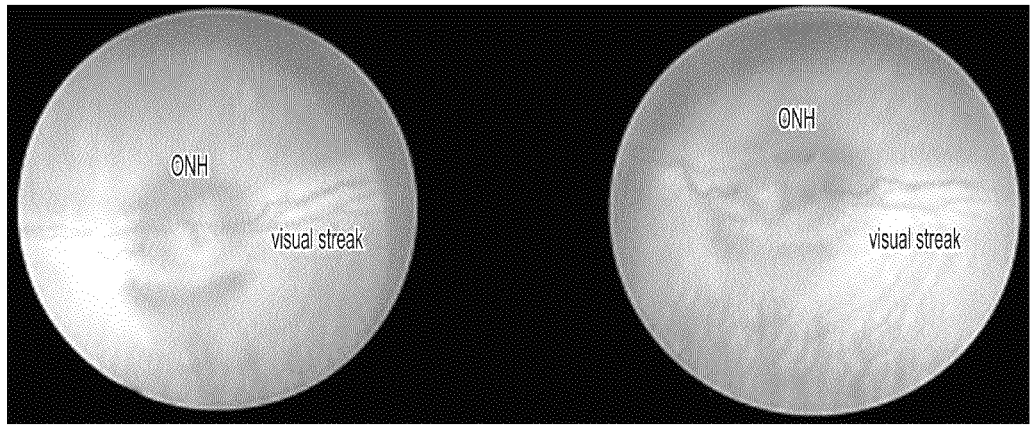
FIG. 6A illustrates a comparative study of rabbit 1105 eye before intravitreal injection and rabbit 1105 eye 14 days after intravitreal injection.
Figure 6B:
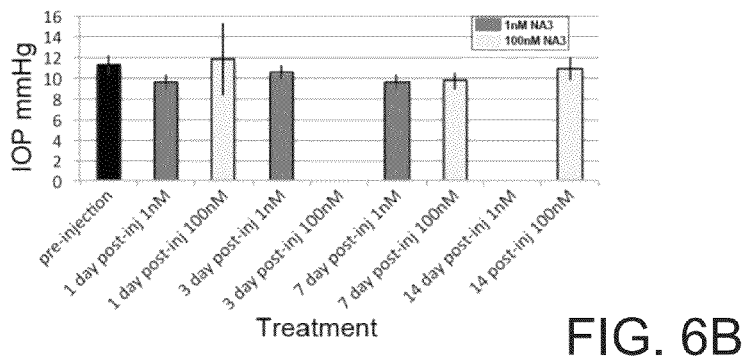
FIG. 6B illustrates change in intraocular pressure (as measured in mm/Hg) before injection and at specified interval times after injection.
Figure 6C:
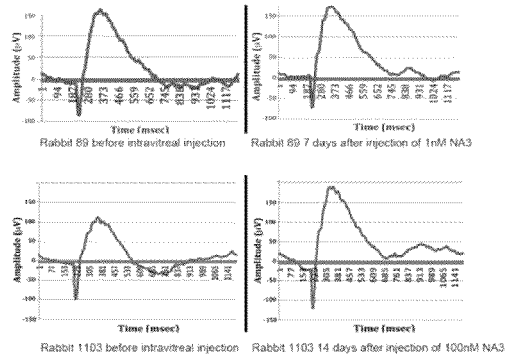
FIG. 6C illustrates comparative data of rabbit (1103) eye before intravitreal injection and rabbit 1103 eye after injection of triantennary N-linked oligosaccharide (NA3) glycan.
Figure 6D:
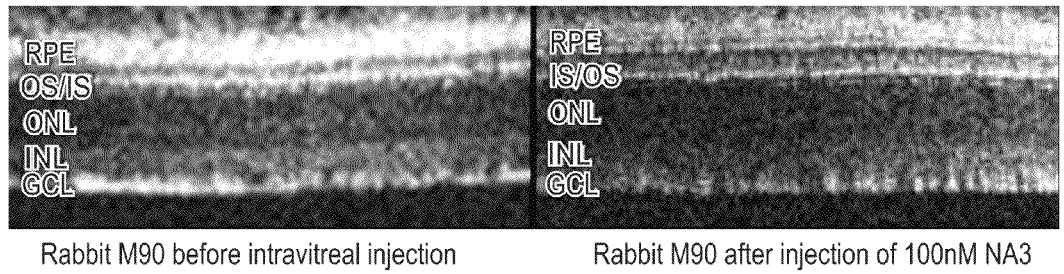
FIG. 6D illustrates rabbit M90 eye before and after injection of 100 mM NA3.
Figure 6E:
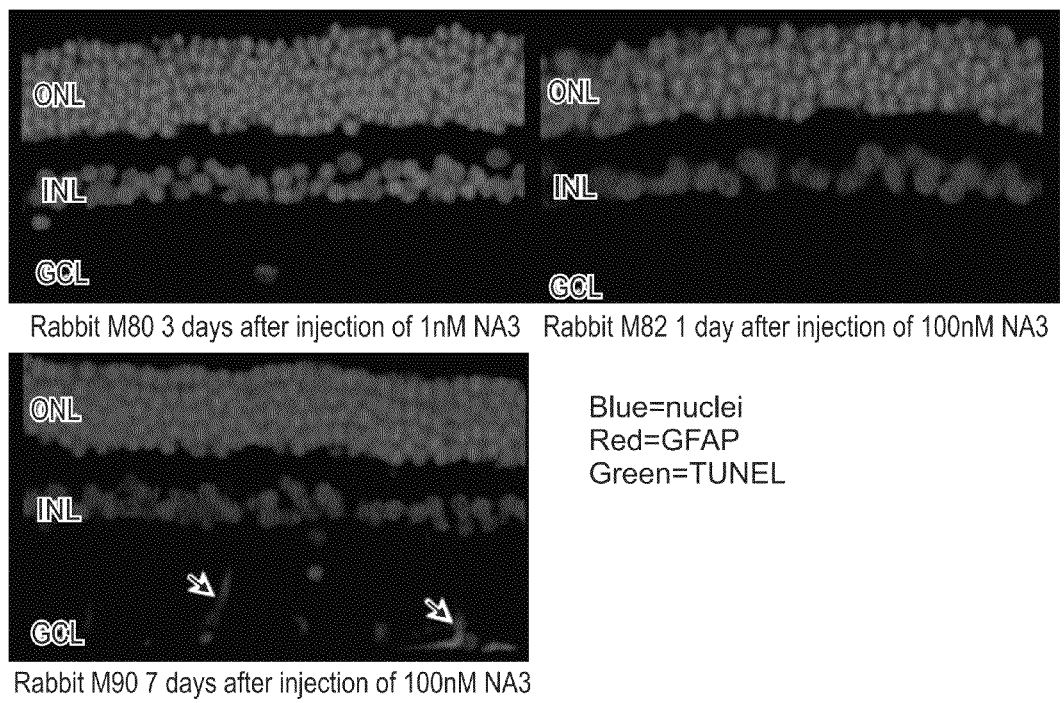
FIG. 6E illustrates rabbit M90 eye after injection of different concentrations (1 nM, 100 nM) of NA3 glycan after specific time intervals (1 day, 3 days and 7 days).
Figure 7A:
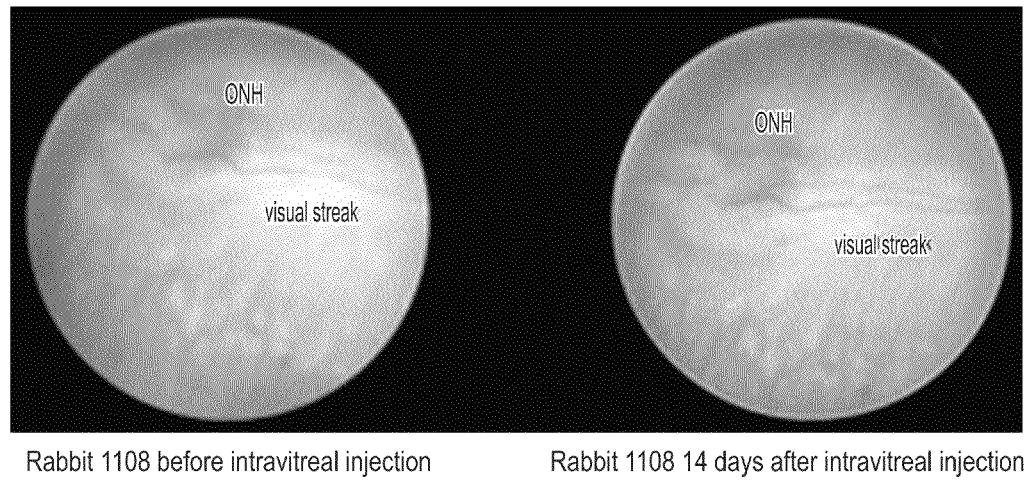
FIG. 7A shows Rabbit 1108 eye before and 2 weeks after intravitreal injection.
Figure 7B:
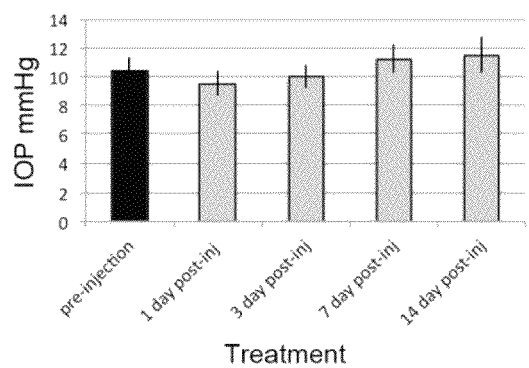
FIG. 7B illustrates the difference in intraocular pressures (IOP as indicated in mm/Hg) measured pre-injection and at several intervals post injection.
Figure 7C:
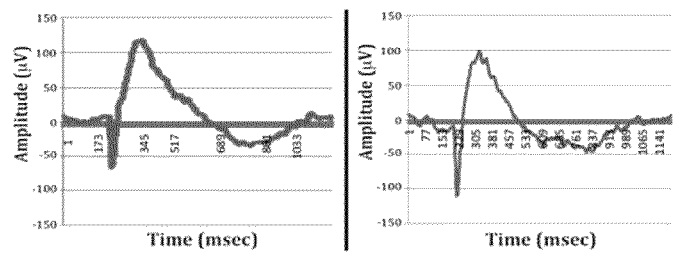
FIG. 7C shows Rabbit 1101 eye before and 2 weeks after intravitreal injection of 10 mg/ml nanoparticles.
Figure 7D:
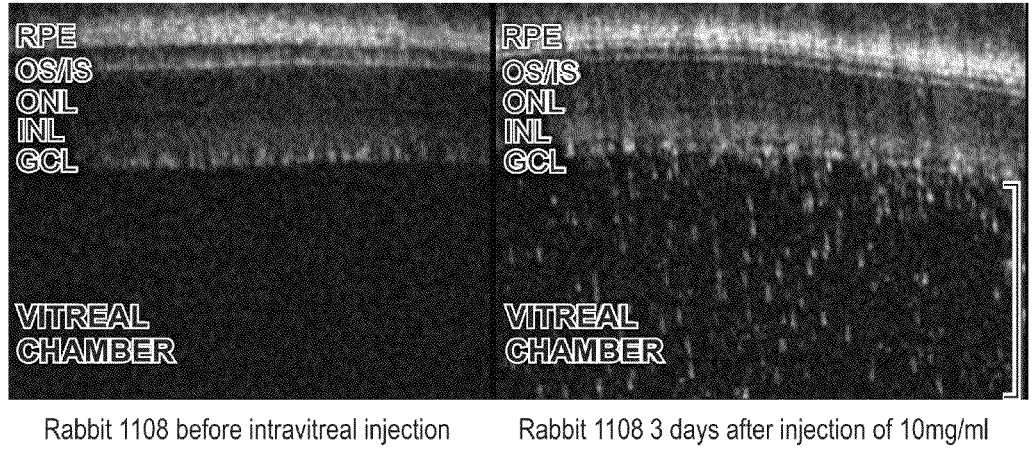
FIG. 7D shows Rabbit 1008 eye before and 3 days after intravitreal injection.
Figure 7E:
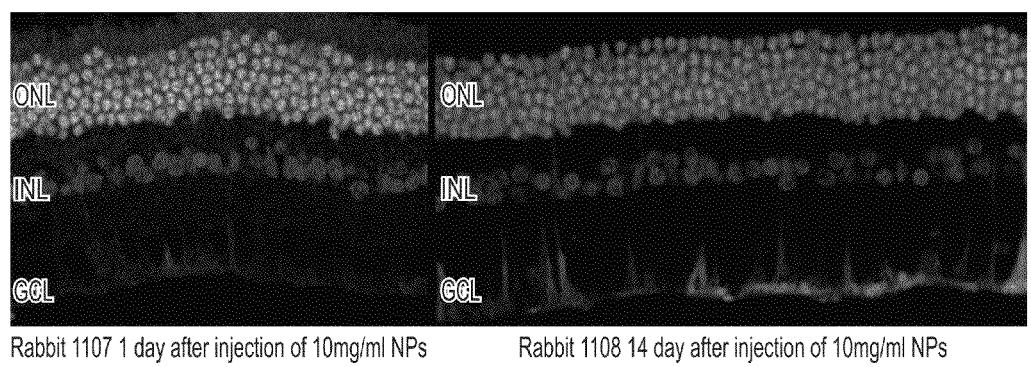
FIG. 7E shows rabbit 1107 eye 1 day and 2 weeks after injection of 10 mg/ml of nanoparticles.

Now referring to FIG. 5, with respect to example 3, eyes exposed to biotinylated glycans showed heavy labeling throughout the retina of all three species tested, *Xenopus laevis* frog, B6 mouse, and human donor eye. Labeling was observed in the area of photoreceptor nuclei in the outer nuclear layer (ONL). The distribution of immunoreactive labeling associated with glycan binding suggested that glycan binds to Müller cells in all species tested.

In further embodiments, FIGS. 6A-E and FIGS. 7A-E provide safety studies for triantennary N-linked oligosaccharide (NA3) and poly(ortho ester) nanoparticles.

Clinical and laboratory exams as shown in FIGS. 6A-E and FIGS. 7A-E include fundus exams, intraocular pressure (TOP) measurements, retinal function—electroretinography (ERG), in vivo retinal structure—optical coherence tomography (OCT), retinal stress—glial fibrillary acidic protein (GFAP) staining and apoptotic cell death—terminal deoxynucleotidyl transferase dUTP nick end (TUNEL) staining.

Referring to FIG. 6A-E, safety example of triantennary N-linked oligosaccharide glycan (NA3) were conducted in NZW rabbits. The effective dose in vitro studies using *Xenopus laevis* frogs is 1 nM. The safety of 1 nM and 100 nM triantennary N-linked oligosaccharide was tested in NZW rabbits. Testing was performed at 1 day, 3 day, 1 week, and 2 weeks after administration. Triantennary N-linked oligosaccharide (NA3) has been shown by FIG. 12 to be non-toxic to the eye at either concentration up to 2 weeks post-administration. Therefore, triantennary N-linked oligosaccharide (NA3) is safe up to 100× the predicted efficacious dose.

Referring to FIG. 7 A-E, safety example of nanoparticles-based delivery system was conducted in NZW rabbits. 1.5 mg/ml of nanoparticles is capable to deliver 1 nM triantennary N-linked oligosaccharide (NA3). NA3 was tested at 1.5 mg/ml and 10 mg/ml dosage, and testing was performed at 1 day, 3 day, 7 day and 14 days after administration. Poly(ortho ester) has been shown by FIGS. 7A-7E to be non-toxic to the eye at either concentration up to two weeks post-administration. Therefore, nanoparticles are an effective means of delivering drugs with zero-order kinetics for long periods of time.

Referring to example 4, novel poly(ortho ester) nanoparticles were generated using a double emulsion solvent evaporation technique to encapsulate water-soluble molecules. Physical characterization of poly(ortho ester) nanoparticles was evaluated using various water-soluble molecules such as, epinephrine, rhodamine 6G and BSA with molecular weights of 333 g/mol, 479 g/mol, and 66000 g/mol respectively. Cytotoxicity and nanoparticle cell uptake.

TABLE 5

Physical properties of empty and loaded poly(ortho ester) nanoparticles.

| POE mol. t. (kDa) | Blank nanoparticles | | | | Water-soluble molecule-loaded nanoparticles | | | | | | |
|---|---|---|---|---|---|---|---|---|---|---|---|
| | Size$^a$ (nm) | PDI | ZP$^a$ (mV) | Yield | Drug | Size$^a$ (nm) | PDI | ZP$^a$ (mV) | Yield | DL % | EE % |
| 5 | 298 | 0.25 | −8.12 | 70.5 | Epi | 241 | 0.112 | −11.5 | 67.5 | 21.1 | 31.7 |
| 22 | 293 | 0.23 | −8.28 | 71.6 | Epi | 242 | 0.104 | −11.9 | 66.8 | 14.3 | 21.4 |
| 22 | — | — | — | — | BSA | 290 | 0.213 | −22.7 | 73.9 | 44.2 | 63.3 |
| 22 | — | — | — | — | Rho | 263 | 0.189 | −15.8 | 71.9 | 2 | 30 |

Studies were also evaluated in detail.
Mol. wt. = molecular weight;
PDI = polydispersity index;
ZP = zeta potential;
DL = drug loading;
EE = entrapment efficiency;
Epi = Epinephrine;
Rho = Rhodamine 6G.
$^a$1 mg/ml nanoparticle emulsion was used to measure the size and zeta potential.

Table 5 summarizes the main physico-chemical characteristics of the poly(ortho ester) nanoparticle formulations. In this example, poly(ortho ester) nanoparticles displayed an average size ranges from 241-298 mu. Epinephrine-loaded nanoparticles were smaller than blank nanoparticles. This size discrepancy may be attributed to the stabilization of the primary W/O emulsion in the presence of epinephrine. This stabilization reduces coalescence of droplets and leads to smaller particle sizes. The epinephrine-induced stabilization is further evidenced by the low polydispersity (PDI) values. Epinephrine-loaded nanoparticles had a lower PDI (≤0.112) than blank nanoparticles (≤0.25). In fact, in all cases, the particle size distribution was quite homogeneous showing low PDI values (≤0.25). There was no significant effect of poly(ortho ester) molecular weight on nanoparticle size. However, by changing the type of encapsulated water-soluble molecule from small molecules to a large molecule, an increase in particle size was observed. All nanoparticles were anionic in nature and the zeta potential changed according to the net charge of the active agent taken for encapsulation. Specifically, the decrease in the negative charge of epinephrine-nanoparticles is likely due to the cationic nature of epinephrine, while the high negative zeta potential of bovine serum albumin (BSA)-nanoparticles may be due to its anionic nature. The yield of the nanoparticles ranged from 66.8% to 73.9%, confirming that the majority of the polymer was converted into nanoparticles. Encapsulations efficiencies of at least 20% are observed with the double emulsion solvent evaporation method used to load hydrophilic drugs. In this example 4, encapsulation efficiencies of drug/dye-loaded nanoparticles, ranged from 21.4% to 63.3%. A higher loading was observed with the large, water-soluble molecule, Bovine serum albumin (BSA) in comparison with a small water-soluble drug/dye. Generally, high encapsulation efficiencies with water-soluble molecules is difficult task to achieve, due to the rapid diffusion of water-soluble drugs from the hydrophobic organic phase into the external aqueous phase that takes place during the preparation of nanoparticle emulsions. In the present example, Bovine serum albumin (BSA), being large in size diffused slowly from the internal aqueous phase and as a result highest encapsulation efficiency was achieved with this molecule.

Figure 8A:
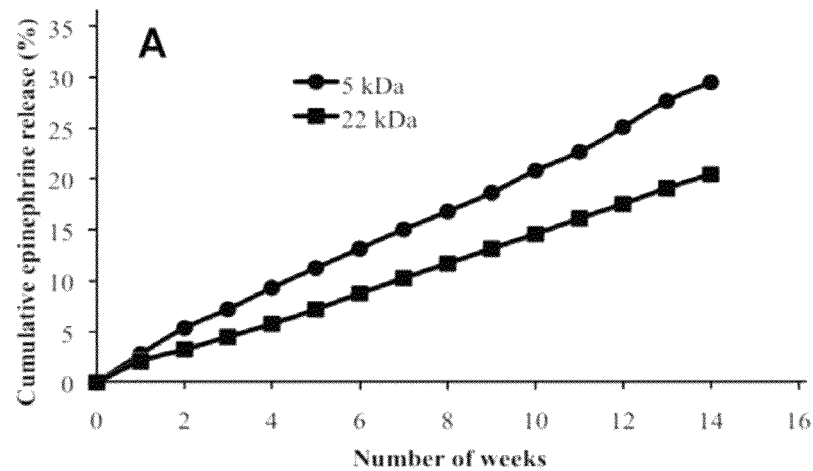
FIG. 8A illustrates in vitro release profiles of epinephrine-loaded nanoparticles

Now referring to FIG. 8A, increasing the molecular weight from 5 kDa to 22 kDa significantly decreased the release rate of epinephrine from poly(ortho ester) nanoparticles (p>0.0001). Nanoparticles of 5 kDa and 22 kDa molecular weight released 29.5% and 20.4%, respectively, of total drug with in 14 weeks at a nearly constant rate. The cumulative drug release was fitted into various release models namely zero-order, first-order, Higuchi's square root plot and Hixson-Crowell cube root plot. The model giving a correlation coefficient close to unity was taken as correct method of release. Zero-order release patterns were observed for both poly(ortho ester) nanoparticles of 5 kDa and 22 kDa molecular weight, with $R^2$ values of 0.998 and 0.999 respectively.

Most drug-loaded particulate formulations show a biphasic release pattern wherein there is an initial burst followed by a sustained release. The high initial release may be due to the presence of free and weakly bound drug on the surface of particulate carriers. However, no such initial burst release was observed in the present case, possibly suggesting the absence of any unbound drug associated with the particles (FIG. 8A). Even though it is a difficult task to design a long-term, zero-order release example for nanoparticle formulations due to a number of practical problems associated with it, poly(ortho ester) nanoparticles are in an excellent position to serve as an ideal drug carrier for intraocular therapies.

Figure 8B:
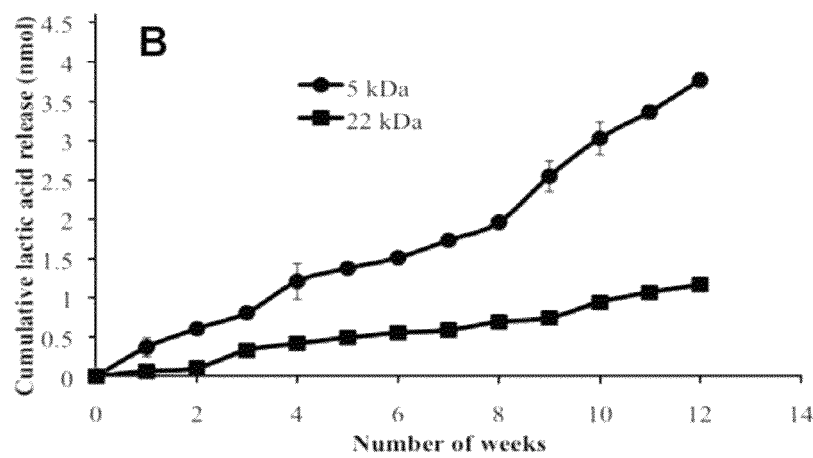
FIG. 8B shows lactic acid release from blank poly(ortho ester) nanoparticles (in pH 7.4 phosphate buffer. Data shown as mean±standard error (n=3).

In a slow eroding poly(ortho ester) polymer, the degradation process is initiated by the breakdown of di-lactate bonds, which simultaneously release free lactic acid. These acid fragments further catalyze ortho ester cleavages and as a resulting in the production of propionic acid. In the same way, poly(ortho ester) nanoparticles also release lactic acid, which indicates the initiation of poly(ortho ester) nanoparticle degradation (FIG. 8B). We measured no lag period before lactic acid was released from poly(ortho ester) nanoparticles (FIG. 8B). In contrast, with poly(ortho ester) polymer there was approximately 20 days of lag time to break down the di lactate bonds. This can be explained by the increase in surface area of poly(ortho ester) nanoparticles in comparison with bolus polymer.

The most significant observation is that lactic acid was released from both nanoparticles of 5 kDa and 22 kDa molecular weight poly(ortho ester) linearly for the entire 12-week period of time with a zero-order release profile (p=0.0002). Nanoparticles of 5 kDa poly(ortho ester) released 3.77 nmol, where as nanoparticles of 22 kDa poly (ortho ester) released 1.17 nmol of lactic acid. These values clearly reflect the degradation rate of both 5 kDa and 22 kDa molecular weight poly(ortho ester) nanoparticles. It was observed that poly(ortho ester) nanoparticles of 5 kDa molecular weight have a faster degradation than 22 kDa molecular weight. It is known from poly(ortho ester) polymers that, the rate of degradation is directly related to the concentration of lactic acid release and as a result, encapsulated drug release observed (Schwach-Abdellaoui, K.; Heller, Gurny, R. *Hydrolysis and erosion studies of autocatalyzed poly(ortho esters) containing lactoyl-Lactyl acid dimers, Macromolecules* 1999, 32, 301-307). Poly(ortho ester) nanoparticles also follow the same trend in lactic acid release and epinephrine release, which reflects poly(ortho ester) nanoparticle degradation.

Figure 9:
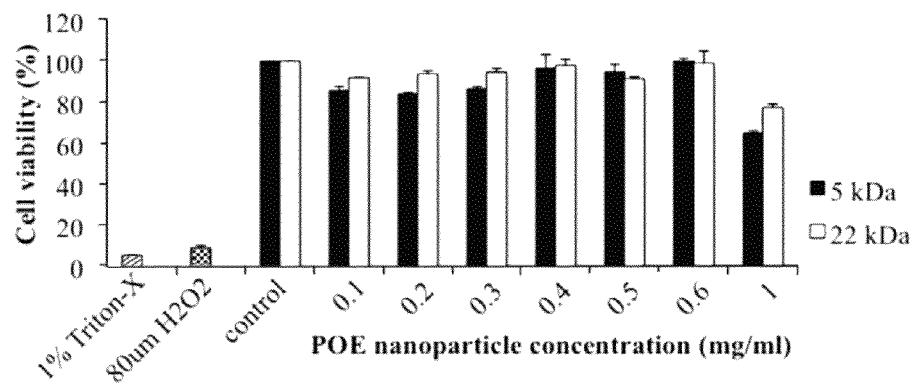
FIG. 9 shows in vitro cytotoxicity of nanoparticles of 5 kDa and 22 kDa molecular weight poly(ortho ester). Data shown as mean±standard error (n=3).

Now referring to FIG. 9 nanoparticles generated using both 5 kDa and 22 kDa molecular weight polymers were observed to have low cytotoxicity. The relative cell viability when exposed to all nanoparticle concentrations was between 84-100% viability, with the exception of 1 mg/ml nanoparticles. Cells exposed to 1 mg/ml showed 65% and 77% cell viability when exposed to nanoparticles made from 5 kDa and 22 kDa molecular weight polymers, respectively. Cell viability of positive controls, 1% Triton-X 100 and 80 μm $H_2O_2$ measured as 5% and 8% viable, respectively. Cell culture medium served as a negative control, which showed 100% cell viability.

Figure 10:
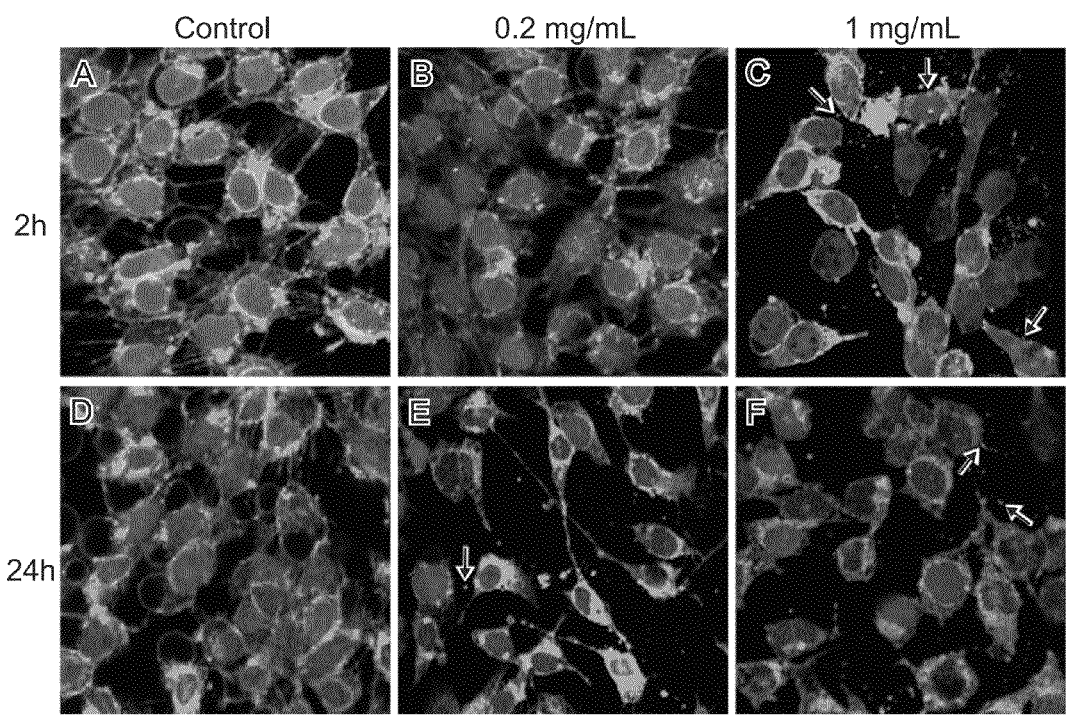
FIG. 10 shows confocal fluorescence microscopy images of Müller cells after exposure to nanoparticles. Cell membranes and nuclei were labeled with OREGON GREEN 488 DHPE (Invitrogen; Grand Island, N.Y.) and TO-PRO-3 IODIDE (Invitrogen; Grand Island, N.Y.) and are shown in green and blue, respectively. Poly(ortho ester) nanoparticles loaded with rhodamine 6G are represented with red color and shown with white arrows.

Now referring to FIG. 10 representative confocal images of Müllner cells exposed to rhodamine 6G-loaded nanoparticles under various conditions are shown. Cells were exposed to rhodamine 6G-loaded nanoparticles, washed only once and imaged to determine if nanoparticles adsorbed to the cell membranes or were internalized. The data shows that the vast majority of the rhodamine 6G-loaded nanoparticles were washed away and did not adsorb to the membranes of the cells irrespective of the concentration of nanoparticles and incubation times used. Of the few nanoparticles that did adsorb, none were internalized by both Müller and HEK-293 cells. In the present example, rhodamine 6G-loaded poly(ortho ester) nanoparticles were anionic with −15.8 mV surface charge. In addition, both Müller cells and HEK-293 have negatively charged cell membrane surfaces Because of this, rhodamine 6G-loaded poly(ortho ester) nanoparticles had very little affinity with either cell line. Unlike cancer therapies, intraocular drug delivery systems should remain extracellular to deliver drugs for prolonged periods so as to avoid repeated intraocular injections.

To further confirm the rhodamine 6G-loaded nanoparticle cell uptake data obtained from confocal images, rhodamine 6G was quantified in both Müller cell and HEK-293 uptake studies, under various experimental conditions (Tables 6 and 7). The amount of rhodamine 6G was quantified in all three washings and cell lysates of both Müller cells and HEK-293. In all cases, most of the rhodamine 6G was observed in preferentially in wash I while only a small quantity was present in wash II. Rhodamine 6G was beyond the limits of detection in both wash III and cell lysates. These quantitative data strongly support the qualitative data, and confirm that poly(ortho ester) nanoparticles were not internalized irrespective of their concentrations, cell lines and incubation time periods.

TABLE 6

Quantification of rhodamine 6G in Muller cell uptake studies.

| Sample (mg/ml) | Incubation time | Wash I* | Wash II* | Wash III | Cells |
|---|---|---|---|---|---|
| 0.2 | 2 h | 93.2% ± 0.05 | n/d | n/d | n/d |
| 1 | 2 h | 94.0% ± 0.14 | 1.90% (0.01 | n/d | n/d |
| 0.2 | 24 h | 96.1% (0.05 | 0.52% (0.03 | n/d | n/d |
| 1 | 24 h | 95.4% (0.16 | 0.80% (0.01 | n/d | n/d |

*Mean ± standard error (n = 3).
n/d denotes not in a detectable range.

TABLE 7

Quantification of rhodamine 6G in HEK-293 cell uptake studies.

| Sample (mg/ml) | Incubation time | Wash I* | Wash II* | Wash III | Cells |
|---|---|---|---|---|---|
| 0.2 | 2 h | 90.5% ± 0.13 | 4.60% ± 0.03 | n/d | n/d |
| 1 | 2 h | 93.2% ± 0.22 | n/d | n/d | n/d |
| 0.2 | 24 h | 92.4% ± 0.14 | 2.80% ± 0.11 | n/d | n/d |
| 1 | 24 h | 92.7% ± 0.062 | 0.12% ± 0.03 | n/d | n/d |

*Mean ± standard error (n = 3).
n/d denotes not in a detectable range.

Figure 11A:
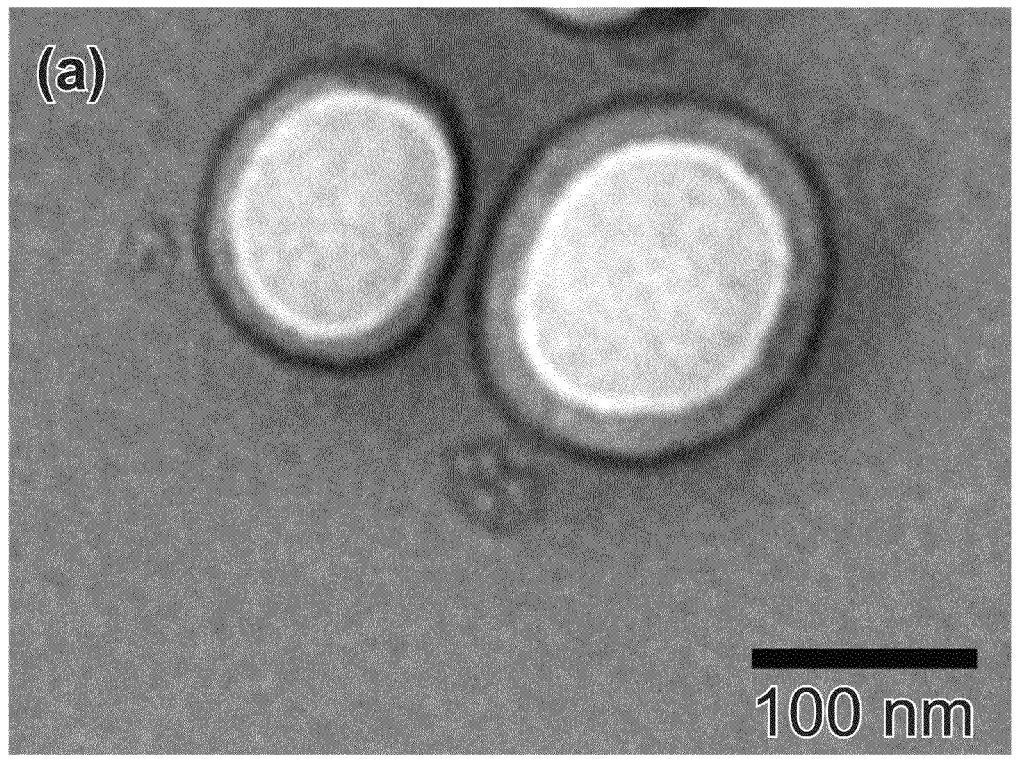
FIG. 11A shows a transmission electron microscopy (TEM) view of the stability of poly(ortho ester) nanoparticles over a period of 50 days.
Figure 11B:
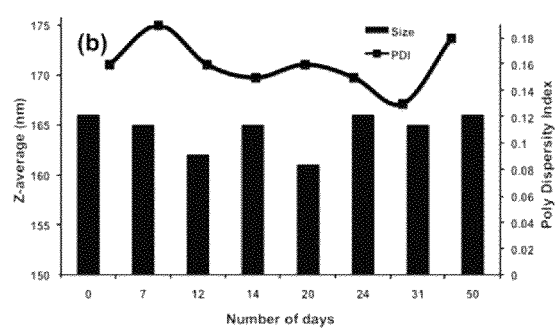
FIG. 11B illustrates stability of poly(ortho ester) nanoparticles over a period of 50 days measured by dynamic light scattering (DLS).

Now referring to FIG. 11B, the stability of nanoparticles emulsions obtained by solvent diffusion method was studied by measuring the size of the nanoparticulate emulsion stored at room temperature. The nanoparticle emulsions were optically transparent and no sedimentation of particles due to agglomeration was observed throughout the 50-day period. Very minute changes in nanoparticles size and PDI values were observed. Mean particle size diameters were measured with in the range from 161 to 166 mu and ≤0.19 PDI value. TEM images were taken on blank nanoparticles after storing them for 6 weeks. FIG. 11A showed the representative image of nanoparticles of 22 kDa poly(ortho ester). Like freshly made nanoparticles, aged nanoparticles were retained within the original size distribution with almost spherical shapes and poly(ortho ester) shells.

Table 8 shows the particle size distributions of the poly(ortho ester) nanoparticles prepared with two different molecular weight polymers, when poloxamer 188 as a stabilizer was used at a constant concentration of 1.25% (w/v) with respect to the amount of internal aqueous phase. Poly(ortho ester) nanoparticles of both 5 kDa and 22 kDa molecular weight showed mean particle size ranging from 151-164 nm and also all nanoparticles had narrow range size distribution, (polydispersity index (PDI) values were less than 0.13). Also, the emulsions of poly(ortho ester) nanoparticles obtained were optically transparent. Since nanoparticles were formed from the emulsion droplets after organic solvent diffusion, their size is dependent on the stability of the emulsion droplets, which collide and coalesce among themselves. When the stabilizer remains at the liquid—liquid interface during the diffusion process, and its protective effect is adequate, nanoparticles will form. Small particle sizes were attributed to both the adequacy of the stabilizer's protection against coalescence, and the low interfacial tension between aqueous and organic phases, resulting from the partially water-soluble nature of ethyl acetate.

High encapsulation efficiencies of at least 98% are observed with the double emulsion solvent diffusion method used to load lipophilic drugs. Efficient encapsulation of the lipophilic drug, celecoxib, was achieved with both 5 kDa and 22 kDa molecular weight poly(ortho ester) nanoparticles. 98.44% and 98.94% entrapment efficiencies were determined, using UV-spectroscopic analysis, for 5 kDa and 22 kDa molecular weight poly(ortho ester) nanoparticles, respectively. This may be explained on the basis of hydrophobicity of the polymer. Poly(ortho ester) used in this example was formed by all hydrophobic units such as, 1,10-decanediol, D,L-lactide and diacetal, and the obtained polymer was highly hydrophobic in nature. Hence, the hydrophobicty of the poly(ortho ester) could have led to increased solid-state solubility of hydrophobic drug in the polymer, resulting in increased entrapment efficiency. Yield of the nanoparticles of 5 kDa and 22 kDa, was high (87-91%), indicating that the most of the polymer was converted into particles.

Figure 12A:
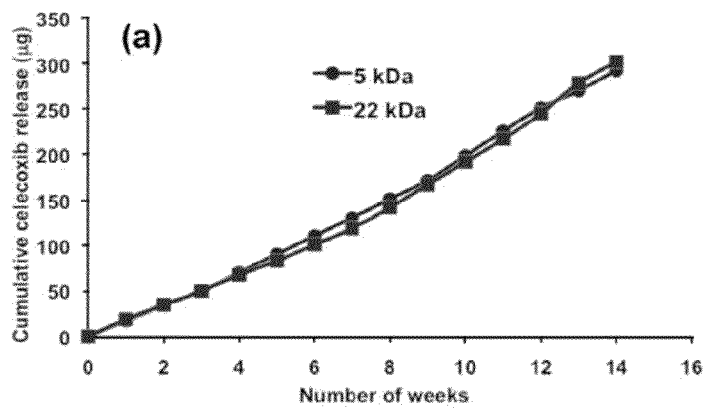
FIG. 12A shows cumulative release profiles of celecoxib in pH 7.4 phosphate buffer

Now referring to FIG. 12A, the in vitro release profile of celecoxib from poly(ortho ester) nanoparticles is shown in. 292 μg and 300 μg of celecoxib was released from nanoparticles of 5 kDa and 22 kDa molecular weight poly(ortho ester) during 14 weeks, without any burst release. In general, most drug delivery systems show a biphasic release pattern wherein there is an initial burst followed by a sustained release. The high initial release may be due to the presence of free and weakly bound drug on the surface of particulate carriers. However, no such initial burst release was observed in the present case, possibly suggesting the absence of any unbound drug associated with the particles.

Despite high encapsulation efficiencies, celecoxib release from nanoparticles was very slow and continuous. Reasons for this sustained release were hydrophobicity of both the polymer and celecoxib, as well as the degradation rate of the polymer. Celecoxib, being hydrophobic in nature, further increases the hydrophobicity of the poly(ortho ester) nanoparticles and causes the slower degradation and simultaneous drug release. The degradation behavior of poly(ortho ester) nanoparticulate system further depends on the degree of hydrophobicity of poly(ortho ester) used for the example. The more hydrophobic the polymer, the slower will be its degradation.

In this example highly hydrophobic and amorphous poly(ortho ester) with very low concentration (5 moles) of lactide groups (which allows water penetration into the poly(ortho ester)) in the polymer skeleton was synthesized. Lactic acid, being hydrophobic makes poly(ortho ester) with D,L-lactide

TABLE 8

Physical properties of blank and celecoxib-loaded poly(ortho ester) NPs.

| | Blank NPs | | | | Celecoxib-loaded NPs | | | | | |
|---|---|---|---|---|---|---|---|---|---|---|
| polymer mol. wt. (Da) | Size [nm] [a] | PDI | ZP [mV] [a] | Yield % | Size [nm] [a] | PDI | ZP [mV] [a] | Yield % | DL % | EE % |
| 5 kDa | 164 | 0.12 | −28.7 | 90.5 | 151 | 0.112 | −32.5 | 87.5 | 64.53 | 98.44 |
| 22 kDa | 161 | 0.08 | −28.5 | 91.66 | 153 | 0.104 | −36.1 | 89.8 | 65.96 | 98.94 | mol. wt.: molecular weight,
Da: Dalton,
PDI: polydispersity index,
ZP: zeta potential,
DL: drug loading,
EE: entrapment efficiency.
[a] 1 mg/ml NP emulsion was used to measure the size and zeta potential.

more hydrophobic and subsequently slows down the degradation process. Therefore, by incorporating small amount of lactide into the poly(ortho ester) polymer, slow degradation rate observed and subsequently controlled and long-term release rate of encapsulated drug can be achieved (Schwach-Abdellaoui, K; Heller; J.; Gurny, R. *Hydrolysis and erosion studies of autocatalyzed poly(ortho esters) containing lactoyl-lactyl acid dimers. Macromolecules* 1999, 32, 301-307), which is desirable for an intraocular therapy to avoid complications caused by frequent intravitreal injections. For long-term release, the desired rate is such that it allows for one full year of continuous zero-order release for an entire year.

The cumulative drug release was fitted into different release models namely zero-order, first order, Higuchi's square root plot and Hixson-Crowell cube root plot. The model giving a correlation coefficient close to unity was taken as order of release. Zero-order patterns were observed for both poly(ortho ester) nanoparticles of 5 kDa and 22 kDa molecular weight, with $R^2$ values of 0.995 and 0.990 respectively ($p<0.0179$). The understanding of the degradation phenomenon of poly(ortho ester) is important as it determines the mechanism of drug release. In general, poly(ortho ester) undergoes surface degradation through heterogeneous hydrolytic erosion, which confines the hydrolysis to the surface of the delivery system and therefore commonly referred to as surface erosion.

This process gives rise to a zero-order drug release for drug delivery systems with constant surface area. The initial degradation product, lactic acid (acidic group) monomer and oligomers thus formed further catalyze the degradation of the parent polymer, a process known as autocatalysis. Release of the entrapped drugs from poly(ortho ester)-based drug delivery systems has been found to occur through a degradation-mediated process.

Figure 12B:
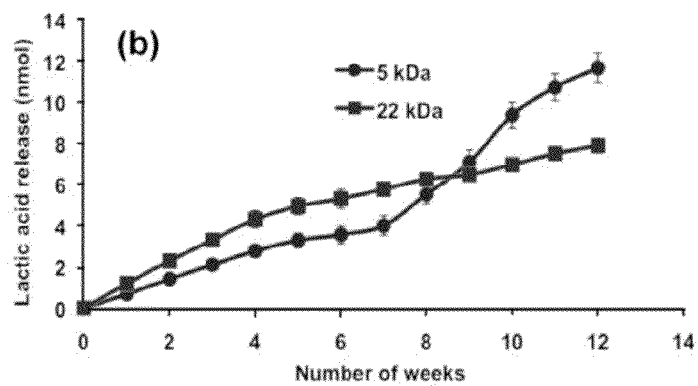
FIG. 12B shows lactic acid release from poly(ortho ester) nanoparticles in pH 7.4 phosphate buffer. Data shown as mean±standard error (n=3).

The surface erosion of poly(ortho ester) takes place by hydrolysis mechanism, which proceeds in three successive steps. In the first step, the lactic acid dimer segment in the polymer backbone hydrolyzes to generate a polymer fragment containing a carboxylic acid end group, which will catalyzes ortho ester hydrolysis. A second cleavage produces free lactic acid, which also catalyzes hydrolysis of the ortho ester links. The hydrolysis of ortho esters then proceeds in two steps, as previously shown, first generates the diol or mixture of diols used in the synthesis and pentaerythritol dipropionate, followed by ester hydrolysis to produce pentaerythritol and propionic acid. Lactic acid release is an indication of poly(ortho ester) weight loss or degradation. Similar to the bulk polymer, poly(ortho ester) nanoparticles too released lactic acid release showing the confirmation of initialization of degradation process. Lactic acid released linearly over 12 weeks from both 5 kDa and 22 kDa poly(ortho ester) nanoparticles and followed near zero-order release (FIG. 12B). Unlike bulk poly(ortho ester), the nanoparticles did not show any lag period in the lactic acid release, which is explained on the basis of the increase in the surface area of the nanoparticles compared to the bulk polymer. Since lactic acid release and celecoxib release from the poly(ortho ester) nanoparticles were constant over a period of time and also there is a direct relation between lactic acid release and degradation, it is confirmed once again that celecoxib release from the poly(ortho ester) nanoparticles was polymer surface erosion controlled.

Figure 13:
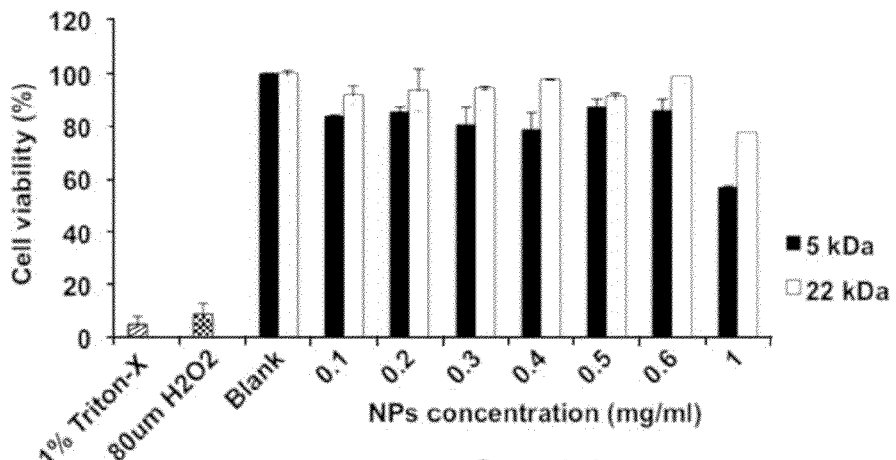
FIG. 13 illustrates the effect of poly(ortho ester) nanoparticles on cell (HEK 293) viability. Data shown as mean±standard error (n=3).

The MTT assay was performed to evaluate the cytotoxicity of poly(ortho ester) nanoparticles to HEK 293 cells (FIG. 13). The results of MTT indicated that poly(ortho ester) nanoparticles did not significantly affect the cell viability after 48 h incubation with HEK 293. Furthermore, the cell viability of 22 kDa molecular weight polymeric nanoparticles concentrations 0.1 mg/ml to 0.6 mg/ml was similar to the negative control group (91-99%), and 77% of cell viability was observed with a concentration of 1 mg/ml. The cell viability of 5 kDa molecular weight poly(ortho ester) nanoparticles concentrations up to 0.6 mg/ml was with in the range of 79-87%, and 57% of cell viability was observed with a concentration of 1 mg/ml. Cell viability of positive controls, 1% Triton-X 100 and 80 µm $H_2O_2$ measured as 5% and 8% viability, respectively. Cell culture medium served as a negative control, which showed 100% cell viability. Nanoparticles prepared with 5 kDa molecular weight poly(ortho ester) show significantly more cytotoxicity in comparison with nanoparticles prepared from 22 kDa molecular weight ($p<0.0035$), which may be explained on the basis of lactic acid release concentrations from poly(ortho ester) nanoparticles. Though the nano-molar concentration of lactic acid is not toxic to intraocular structures, cells are sensitive and shown little toxicity. Hence, the cell viability data suggests that all poly(ortho ester) nanoparticles, except 1 mg/ml concentration of 5 kDa polymeric nanoparticles, had low cytotoxicity to the HEK 293 cells with concentrations of up to 1 mg/ml.

Figure 14:
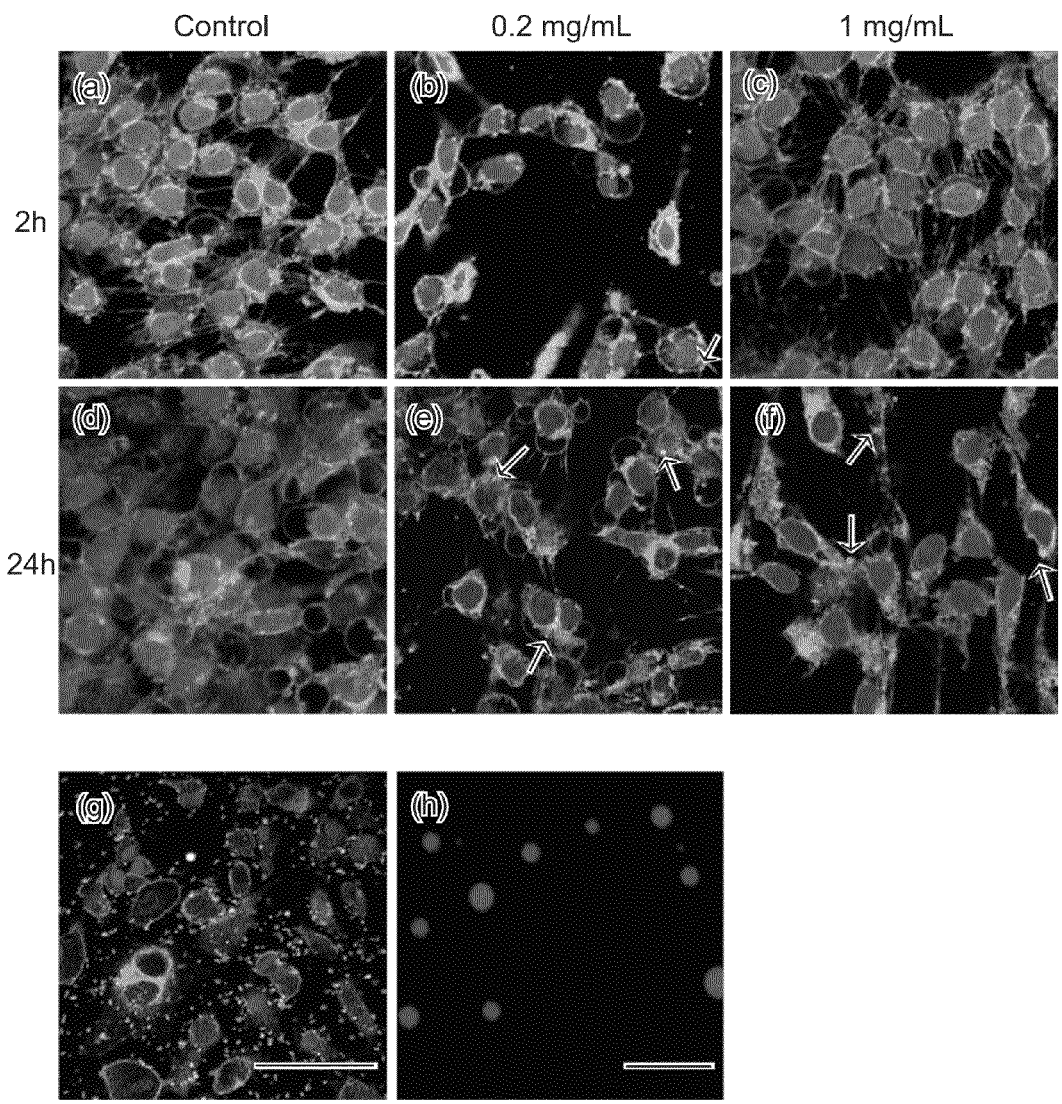
FIGS. 14 A-F illustrate confocal fluorescence microscopy images of Müller cells after exposure to Nile red-loaded poly(ortho ester) nanoparticles after washing.

Now referring to FIG. 14 representative images of Nile red-loaded nanoparticles uptake in Müller cell line at various experimental conditions was shown in Müller cell and HEK 293 cells were used to evaluate the cellular uptakes of Nile red-loaded poly(ortho ester) nanoparticles. Müller cells were selected as an in vitro model with the aim of delivering poly(ortho ester) nanoparticles via an intravitreal injection for intraocular therapy. HEK 293 cells were selected in order to investigate if they differently uptake poly(ortho ester) nanoparticles, thus potentially displaying different toxicity profiles. After exposure to Nile red-loaded nanoparticles, cells were imaged before and after (FIG. 14A-E) washing one time with phosphate buffered saline, to determine if nanoparticles adhered to the cell membranes or were internalized. It is evidenced from FIG. 14A-E, that in all cases the vast majority of the Nile red-loaded nanoparticles were washed away and did not adhere to the membranes. Of the few that did adhere, none were internalized by either Müller or HEK 293 cells (data not shown). Even after increasing the incubation time from 2 h to 24 h and nanoparticles concentrations from 0.2 mg/ml to 1 mg/ml, nanoparticle uptake was not seen. Even though many Nile red-loaded nanoparticles were present prior to washing, none of the nanoparticles were internalized (FIG. 14G), which is explained on the basis of the negative surface charge of both nanoparticles and cell membranes. In the present example, the high negatively charged surfaces of poly(ortho ester) nanoparticles may limit the interactions between nanoparticles and the cell membrane. For example, the zeta-potentials of 5 kDA and 22 kDa molecular weight poly(ortho ester) nanoparticles were measured as −28.7 mV and −28.5 mV, respectively. Moreover, both Müller and HEK 293 cell membrane surfaces are negatively charged. The present drug delivery systems are preferably administered in a sterile form. For example, the present drug delivery systems, or compositions containing such systems, may be sterile when stored. Any routine suitable method of sterilization may be employed to sterilize the drug delivery systems. For example, the present systems may be sterilized using radiation such as by gamma irradiation or other method known to one skilled in the art.

In summary, nanoparticles and cell membrane surfaces with negative charges repel each other and do not get adsorbed on the membranes for further internalization. Thus, poly(ortho ester) nanoparticles may have a favorable surface charge, which resists cell uptake. This property is highly desirable for an intraocular drug delivery carrier to maintain the efficient therapeutic levels for prolonged periods and the slower degradability further minimizes the repeated intraocular injections.

Example 1

In a preferred embodiment, hydrophilic drug loaded nanoparticles were formulated using a double-emulsion solvent evaporation system.

Typically, 2-4 mg of hydrophilic drug were dissolved in 0.1 ml distilled water, and 30 mg of poly(ortho ester) were dissolved in 1 ml of Dichloromethane:acetone (8:2) solvent mixture containing 0.05% Pluronic F68. The aqueous drug solution was added to the poly(ortho ester) organic solution and a water-in-oil (W/O) emulsion formed by sonication over an ice bath using a probe-type sonicator operating at 60% amplitude intensity for 2 min. This W/O emulsion was further added to a 2.5% poly(vinyl alcohol) aqueous solution with sonication to achieve the water-in-oil-in-water [(W/O)/W] double emulsion system. The organic solvents were allowed to evaporate while being stirred first at atmospheric pressure for 16 h and then at gradually reduced pressure (from 100 mmHg to 30 mmHg) for 2 h. The solidified nanoparticles were collected by ultracentrifugation at 30 000×g for 20 min and washed three times with distilled water to remove residual poly (vinyl alcohol) and any free drug. The final product was dried by lyophillization.

For a typical formulation of the (double emulsion solvent diffusion (DESD)-hydrophilic (HP), 20 mg of hydrophilic drug was dissolved in 200 µl of distilled and deionized water, which was further emulsified in 1 ml of ethyl acetate containing 30 mg of poly(ortho ester) polymer and 30 mg of PLURONIC F-68 (Sigma Aldrich; St. Louis, Mo.) by sonication over an ice bath using a probe sonicator at 20 W output for 1 min. 30 s. The resulting primary w/o emulsion was added to 4 ml of deionized water and was sonicated for 90 sec at 50% amplitude over an ice bath to form the w/o/w double emulsion. The remaining steps were carried out as mentioned above.

The lipophillic drug was encapsulated in poly(ortho ester) nanoparticles by using the double emulsion solvent diffusion method (DESD-lipophilic). 50 mg of poly(ortho ester) was dissolved in five ml of ethyl acetate. The organic phases were added into 10 ml of an aqueous phase containing 1.25% of PLURONIC F-68 (Sigma Aldrich; St. Louis, Mo.) as a stabilizer. This mixture was kept for 4 min. to attain mutual saturation of organic and aqueous phases, then the mixture was emulsified for 4 min. with a probe-type sonicator (probe-tip diameter: 1.3 cm, Sonics & Materials Inc., Danbury, Conn., USA) operating at 60% amplitude intensity. In order to allow diffusion of the organic solvent into water, a constant volume (40 ml) of Milli-Q water was subsequently added to the o/w emulsion under moderate magnetic stirring, leading to the formation of hydrophobic drug loaded poly(ortho ester) nanoparticles. The remaining steps were essentially as described above.

Figure 1B:
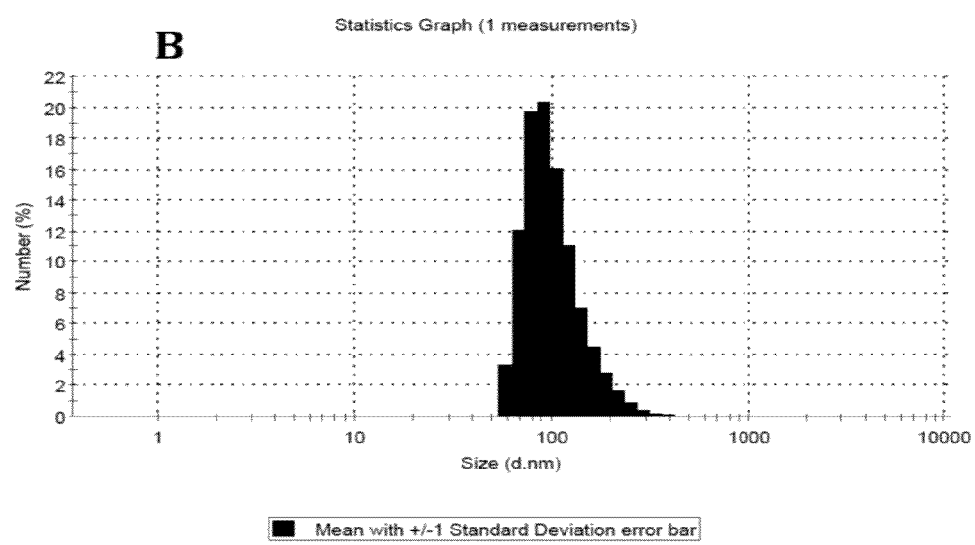
FIG. 1B shows the narrow particle size distribution of 22 kD double emulsion solvent diffusion-nanoparticles.

The size and charge of the poly(ortho ester) nanoparticles were measured using a ZETASIZER (Malvern; Worcestershire, United Kingdom) and are shown in FIG. 1 and Table 9.

The double emulsion solvent diffusion method generated smaller and slightly more anionic nanoparticles than those generated by the double emulsion solvent evaporation (DESE) method. A low polydispersity index (PDI) of 0.086 to 0.119 (Table 9) was obtained for both types of nanoparticles, which indicates a narrow size distribution of the nanoparticles, which allows for a homogeneous distribution.

TABLE 9

Physical characterization of DESE-nanoparticles and DESD-nanoparticles.

| | MW of polymer | Size (nm) | PDI | Charge | Drug loading | Encapsulation efficiency (%) |
|---|---|---|---|---|---|---|
| DESE-NP (epinephrine) | 22 kD | 242 | 0.104 | −7.91 | 14.27% | 21.40% |
| | 5 kD | 241 | 0.112 | −7.91 | 21.11% | 31.66% |
| DESD-NP (celecoxib) | 22 kD | 162 | 0.119 | −28.7 | 65.96% | 98.94% |
| | 5 kD | 165 | 0.086 | −28.7 | 64.53% | 98.44% |

Now referring to Table 10, New DESD method was used to load nanoparticles with hydrophilic drugs. The average size of the nanoparticles is 188 mm, which is smaller than the double emulsion solvent evaporation (DESE) nanoparticles shown in Table 9. The smaller nanoparticles are easier to perform. However, the PDI or range of nanoparticle size is greater.

TABLE 10

Physical characterization of epinephrine-loaded nanoparticles prepared by new DESD Method.

| | Size | PDI | Charge | Drug loading | Encapsulation efficiency (%) |
|---|---|---|---|---|---|
| DESD-NP (Epinephrine) | 188 nm | 0.384 | −38 mV | 15% | 26.28% |

To demonstrate the utility of poly(ortho ester) as nanoparticles, epinephrine, a model hydrophilic drug, was loaded in double emulsion solvent evaporation (DESE)-nanoparticles and celecoxib, a hydrophobic drug, into double emulsion solvent diffusion (DESD)-nanoparticles. The encapsulation efficiency was very high in double emulsion solvent diffusion-nanoparticles; almost the entire drug used for loading was encapsulated in the nanoparticles (Table 9). To increase the encapsulation efficiency in double emulsion solvent evaporation (DESE)-nanoparticles, a small modification was made by increasing the internal aqueous phase to form a W/O primary emulsion. By doing so, the drug loading percentage was increased from 21.4% to 44.24% and the encapsulation efficiency from 31.66% to 63.76% (see Table 11).

TABLE 11

Effect of internal aqueous phase volume on BSA loading in double emulsion solvent evaporation (DESE)-prepared nanoparticles. Only 22 kD polymer was used in these studies.
EXAMPLE 2

| Initial amount of BSA | Loaded amount of BSA | Drug loading % | Encapsulation efficiency |
|---|---|---|---|
| 20.818 | 13.274 | 44.24% | 63.76% |
| 9.795 | 4.966 | 16.10% | 50.70% |
| 4.134 | 2.136 | 7.12% | 51.67% |
| 2.342 | 1.483 | 4.94% | 63.31% |

Materials.

Poly(vinyl alcohol) (PVA), didodecyldimethylammonium bromide (DMAB), sodium dodecyl sulfate (SDS), 1,10 decanediol, D,L-Lactone, poloxamer 188, vancomycin hydrochloride were obtained from Sigma Aldrich (St. Louis, Mo.). 3,9-divinyl-2,8,10-tetraoxaspiro[5.5]undecane was obtained from AK Scientific Inc., USA. Analytical grade solvents such as, ethyl acetate (EA), Dichloromethane (DCM), methyl ethyl ketone, acetone and chloroform were purchased from Sigma Aldrich (St. Louis, Mo.) and used as obtained. Poly(ortho ester) polymer was synthesized and characterized as described in the literature (Schwach-Abdellaoui, K.; Heller, J.; Gurny, R. *Synthesis and characterization of self-catalyzed poly(ortho-esters) based on decanediol and decanediol-lactate; Jthenal of Biomaterial Science Polymer Edit.* 1999, 10, 375-389). Deionized water (DIW) was used in all experiments.

Preparation of Poly(Ortho Ester) Nanoparticles

Double emulsion solvent diffusion (double emulsion solvent diffusion-hydrophilic) method to encapsulate hydrophilic drugs. The preparation of poly(ortho ester) nanoparticles by using double emulsion solvent diffusion-hydrophilic method (Cohen-Sela, E.; Chorny, M.; Koroukhov; Danenberg, H. D.; Golomb, G, *A new double emulsion solvent diffusion technique for encapsulating hydrophilic molecules in PLGA nanoparticles, jthenal of controlled release*, 133, 2009, 90-95) with some modifications, is as follows: 30 mg of poly(ortho ester) (3%) was dissolved in 1 ml of various organic solvents (ethyl acetate, dichloromethane and methyl ethyl ketone). The organic phase was added to an aqueous phase containing various stabilizers. After mutual saturation of organic and aqueous phases, the mixture was emulsified for 90 S with a probe-tip sonicator (probe-tip diameter: 1.3 cm, Sonics & Materials Inc., Danbury, Conn., USA) operating at 65% amplitude intensity. In order to allow for diffusion of the organic solvent into water, a constant volume (6 ml) of water containing 2.5 of poly(vinyl alcohol) was subsequently added to the w/o emulsion under moderate magnetic stirring, leading to the formation of poly(ortho ester) nanoparticles. The organic solvent was allowed to evaporate overnight by stirring over a magnetic stir plate. Nanoparticles thus formed were collected by ultracentrifugation at 20,000 rpm, 20 min, 25° C., and then washed three times with distilled water to remove unincorporated drug and emulsifiers. The final product was dried by lyophilization at 0.002 mbar, −50° C. for 48 hthes on FREEZONE (Labconco Corporation, Kansas, Mo.).

Example 3

A novel glycan binding protein thought to be a cell surface receptor has been discovered in the retina. An issued U.S. Pat. No. 8,092,825 (hereby specifically incorporated by reference in its entirety) disclosed methods of treatment for retinal diseases and conditions including age-related macular degeneration, genetic-based retinal degenerations and retinal detachment.

Methods for intraocular injections rabbits or mice are anesthetized with an intramuscular injection of ketamine/xylazine/acepromazine cocktail or intraperitoneal injection of Avertin or inhalation of isoflurane, Corneas are anesthetized with 0.5% proparacaine. Pupils are dilated with Cyclomydril. A small incision is made in the conjunctiva and a 30 awg needle is inserted to puncture the sclera below the ora serrata. Triantennary N-linked oligosaccharide (NA3), blank nanoparticles and NA3-loaded nanoparticles are injected into the superior temporal aspect of the vitreal cavity of the left eyes. With the assistance of a high-powered dissecting scope, a transcleral approach will be utilized to deliver the substance (30 μl for rabbits and 2 μl for mice) using a 10 μl Hamilton syringe with a 0.5 in 30 awg beveled needle. The target concentration of triantennary N-linked oligosaccharide (NA3) in the vitreous is 1-10 nM.

Methods for clinical examinations to perform the clinical exams: rabbits or mice are lightly anesthetized as above. The anterior segment of the eye is examined using a Haag-Streit slit-lamp biomicroscope. Images of these structures are recorded with a Canon GL1 digital video camera. The cornea is examined for clarity and possible neovascularization; the lens is examined for clarity, and the iris is evaluated for depigmentation or inflammation Immediately after the slit lamp exam, pupils are dilated with Cyclomydril to facilitate examination of the posterior segment. The fundus is examined by indirect ophthalmoscopy and photographs ware taken with a Kowa Genesis small animal fundus camera with the assistance of a condensing lens. Full-field ERGs are recorded. Briefly, animals are dark-adapted overnight and anesthetized. Pupils are dilated with cyclomydril. A gold ring electrode contacting the cornea through a layer of methylcellulose is used to record the response from the retina, while a needle electrode placed in the cheek and tail serves as reference and ground, respectively. Each animal is placed in front of a Ganzfeld bowl (Diagnosis LLC system) that presents a series of flashes with increasing intensity (−3.0 to 2.1 log cd sec/m2). Amplitude and implicit time measurements are recorded and compared between triantennary N-linked oligosaccharide (NA3) or nanoparticles-injected and saline-injected eyes of each animal. Statistical analysis of the relationship between amplitude and intensity is performed using repeated measure ANOVA with an a level of 0.05. We use ocular coherence tomography (OCT) imaging to assess retinal structure in vivo. Briefly, animals are anesthetized and eyes will be dilated as above. Corneas are moistened with Systane Ultra (Alcon). Imaging is performed using the Bioptigen ultra high-resolution OCT system (Bioptigen, Research Triangle Park, N.C.) using the pediatric human or mouse probe, as appropriate. Calibrated digital calipers are used to measure the thickness of retinal layers.

Methods of laboratory exams for structural analysis: eyes are fixed in a mixed aldehyde (2% glutaraldehyde, 2% paraformaldehyde) and embedded in Epon 812 using the published protocols (Jablonski M M Tombran-Tink J, Mrazek D A, Iannaccone A. (2000) *Pigment epithelium-derived factor supports normal development of photoreceptor neurons and opsin expression after RPE removal. J. Neurosci.* 20:7149-7157.). Toluidine blue stained 1 μm sections will be used to look for gross structural abnormalities and thin sections will be used to analyze the detailed structure of the adherens junctions. For immunohistochemical localization of retinal stress proteins (glial fibrillary acid protein (Jablonski M M and Iannaccone A. (2001) *Lactose Supports Müller Cell Protein Expression Patterns in the Absence of the Retinal Pigment Epithelium. Mol. Vis.* 7:27-35), eyes will be fixed in 2% paraformaldehyde. The anterior segment and lens will be removed and the remaining eyecup will be embedded in OCT embedding compound and 12 um thick sections will be taken. The standard methodologies (Nookala S, Gandrakota R, Wohabrebbi A, Wang X, Howell D E, Giorgianni F, Beranova-Giorgianni S, Desiderio D M, Jablonski M M (2010) *In Search of the Identity of the XAP-1 Antigen: A Protein Localized to Cone Outer Segments. Invest Ophthalmol Vis Sci.* 51:2736-2743), including fluorescent secondary antibodies and confocal microscopy, will be used to localize the antigens in retinas. Terminal deoxynucleotidyl transferase dUTP nick end labeling (TUNEL) staining, to detect apoptotic cells, will be performed using DeadEnd Fluorometric TUNEL System following manufacturer's specifications.

Example 4

Poly(Ortho Ester) Nanoparticle-Based Targeted Intraocular Therapy for Controlled Release of Hydrophilic Molecules Development of an efficient intraocular drug delivery nano-system remains the most difficult challenge to attain a prolonged therapeutic effect at the site of drug action. The purpose of this work was to develop a biodegradable, long-term sustained release, and biocompatible nanoparticulate system to treat various intraocular diseases. To attain this objective, poly(ortho ester) a hydrophobic, surface erodible and non-toxic polymer, was selected for the fabrication of nanoparticles for the first time using a double emulsion solvent evaporation (DESE) method. The influence of poly(ortho ester) molecular weight on particle size, polydispersity index, zeta potential, drug content, in vitro release, degradation, in vitro cytotoxicity and cell uptake studies was investigated. Drug-loaded nanoparticles had a spherical shape with an average particle diameter from 241 to 298 nm and zeta potential values from −8 to −11 mV. Encapsulation efficiencies ranged between 21 and 63%, depending on the type of the water-soluble molecule used. Approximately 20-30% of the loaded drug was released over a period of 14 weeks. The drug release and degradation profiles of nanoparticles followed perfect zero-order kinetics confirming the poly(ortho ester)-surface erosion mechanism. In vitro cytotoxicity and cell uptake studies revealed the cytocompatible nature and non-endocytic behavior of poly(ortho ester) nanoparticles. Collectively, poly(ortho ester) nanoparticles are very promising vehicle for sustained delivery of therapeutics to the back of the eye.

Materials and Methods

Materials

Poly(vinyl alcohol) (PVA), 1,10 decanediol, D,L-Lactone, poloxamer 188, 3-(4,5-dimethylthiazol-2-yl)-2,5-diphenyltetrazolium bromide (MTT), rhodamine 6G and (−)-epinephrine (+)-bitartrate salt, acetone, dichloro methane, tetrahydrofuran and dimethyl sulfoxide (DMSO) were obtained from Sigma Aldrich (St. Louis, Mo.). 3,9-divinyl-2,4,8,10-tetraoxaspiro[5.5]undecane was obtained from AK Scientific Inc., USA. Bovine serum albumin (BSA) was purchased from Electron Microscopy Sciences, (Hatfield, Pa.). Lactate assay kit was purchased from BioVision (Milpitas, Calif.). Dulbecco's Modified Eagle Medium was purchased from Fisher Scientific (Fair Lawn, N.J.). OREGON GREEN 488 DHPE and TO-PRO-3 IODIDE were purchased from Invitrogen (Grand Island, N.Y.). Human Embryonic Kidney cell lines (HEK-293), Eagle's minimal essential medium (EMEM), were obtained from ATCC (Manassas, Va.). rMC-1 Müller cells (Müller cells) were generously provided by Dr. Vijay Sarthy (Northwestern University).

Poly(ortho ester) nanoparticle preparation involves, 1,10-decanediol-lactate (2.5×10 mol) 1,10-decanediol (47.5×10-3 mol) were dissolved in anhydrous tetrahydrofuran. Subsequently, 3,9-diethylidene-2,4,8,10-tetraoxaspiro[5.5]undecane (DETOSU) (50×10-3 mol) was added under argon atmosphere and the polymerization initiated by the addition of six drops of p-TSA w/w I % solution in THF. The exothermic reaction produced polymer almost spontaneously. The stirring was maintained for 1 h at room temperature and the polymer then precipitated with methanol containing five drops of TEA to stabilize the polymer. After isolation, the polymer was dried at 40° C. under vacuum for 48 h.

Blank poly(ortho ester) nanoparticles were prepared using a water-in-oil-water [(W/O/)W] double emulsion solvent evaporation technique with minor modifications (Song, C. X.; Labhasetwar, V.; Murphy, H.; Qu, X.; Humphrey, W. R.; Shebuski, R. J.; Levy, R. J. Formulation and characterisation of biodegradable nanoparticles for intravascular local drug delivery. J. Control. Release 1997, 43, 197-212). Briefly, poly(ortho ester) (90 mg) and poloxamer 188 (1.5 mg) was dissolved in 3 ml of 8:2 dichloromethane and acetone mixture. The organic mixture was added to 300 (1 of an aqueous solution containing 2.5% of w/v poly(vinyl alcohol) and sonicated over an ice bath using a micro tip probe sonicator S-4000; (Misonic, Inc., Newtown, Conn.) at 65% intensity for 90 sec to form a WO primary emulsion. This primary emulsion was added drop wise under sonication to 18 ml of aqueous solution containing 2.5% w/v poly(vinyl alcohol) to form a water in oil in water secondary emulsion. The organic solvents were allowed to evaporate overnight by stirring over a magnetic stir plate. Nanoparticles thus formed were collected by ultracentrifugation, WX ULTRA 80 (Thermo-Scientific Sorvall Ultracentrifuge, Asheville, N.C., USA) at 20,000 rpm, 20 min, 25° C. and then washed three times with distilled water to remove unincorporated drug/dye and emulsifiers. The final product was dried by lyophilization at 0.002 mbar, −50° C. for 48 h FREEZONE (Labconco Corporation, Kansas, Mo.). Drug/dye-loaded nanoparticles were also prepared in the same method mentioned above, where drug (20 mg)/dye (2 mg) was dissolved in inner aqueous solution.

Particles were characterized by dynamic light scattering (DLS) and transmission electron microscopy (TEM). DLS measurements were conducted with particle suspensions (1 mg/ml) in MILLIPORE water (Millipore Corp, Billercia, Mass.) with a Malvern Nano-ZS (Malvern Instruments, Worcestershire, UK). The morphology of poly(ortho ester) nanoparticles was documented using a transmission electron microscope (JEM-2000 EX II Electron Microscope, JEOL, LTD, Tokyo, Japan) using an acceleration voltage of 60 kV. Two microliters of poly(ortho ester) nanoparticles (0.1 mg/ml) were placed at the center of a copper grid and dried in a dessicator for 24 h. Grids were visualized under the electron microscope at a magnification of 100,000×.

The encapsulation efficiencies of epinephrine, rhodamine 6G and BSA in drug-loaded nanoparticles were determined by dissolving 10 mg of drug-loaded nanoparticle powder in 2 ml of dimethylsulfoxide (DMSO) deionized water (DIW) (1:1). Samples were rotated for at least 24 h at 50 rpm to ensure complete dissolution in aqueous DMSO solution. Blank nanoparticles were treated identically. The concentration of epinephrine, and BSA in the resulting solution was determined by measuring the absorbance at 230 nm and 280 nm respectively, in a spectrophotometer (MQX 200, Bio-Tec Instruments, Winooski, Vt., USA). The rhodamine 6G concentration was measured at excitation/emission=528 nm/1560 nm using micro plate reader (FLx800, BioTek Instruments, Winooski, Vt., USA). The obtained values were then subtracted from the absorbance values of blank poly(ortho ester) nanoparticles. All samples were analyzed in triplicate. A dialysis technique was adapted to carry out the release experiments. Epinephrine release profiles were determined by suspending 30 mg of drug-loaded nanoparticles in 500 µl of phosphate buffered saline (pH 7.4). Samples were incubated at 37° C. while shaking at 50 rpm in an incubator shaker (C 24, New Brunswick Scientific, NJ). Every day, the supernatant was removed and replaced with fresh buffer. The concentration of epinephrine in the supernatant was determined using the UV detection method described above. The absorption of supernatant collected from the blank poly(ortho ester) nanoparticles was negligible at 230 nm throughout the release example. The linear range of the calibration curve was between 2-60 mg/ml and correlation coefficient of the standard curve was 0.9997±0.00026. The amount of drug in each sample was summed with the amount from all previous time points to obtain the cumulative drug release amount. The total was then divided by the actual amount of drug in the nanoparticles to calculate the cumulative drug release percentage. Each release experiment was performed in triplicate.

Lactic acid release from the poly(ortho ester) is a sign of the initialization of polymer degradation. Because of this, quantification of lactic acid released from poly(ortho ester) nanoparticles is very essential to determine their degradation. The amount of lactic acid release was quantified by using lactate assay kit (BioVision Inc., Milpitas, Calif.) following manufacturer's specifications. In vitro cytotoxicity of nanoparticles was evaluated using an MTT assay (Zhang, Y.; Zhuo, R. *Synthesis, characterization, and in vitro 5-Fu release behavior of poly(2,2dimethyltrimethylene carbonate)-poly(ethylene glycol)-poly(2,2-dimethyltrimethylene carbonate) nanoparticles. Jthenal of Biomedical Materials. Research. Part A,* 2006, 76, 674-680) with minor modifications. Briefly, HEK-293 cells were seeded (4400 cells/well) and 100 µl of diluted nanoparticle (0.1, 0.2, 0.3, 0.4, 0.5, 0.6, and 1 mg/ml) emulsions and positive controls, 1% Triton-X 100 and 80 µm H2O2 were added to each well and incubated with the cells for 48 h before being replaced by 160 µl of EMEM. Forty microliters of MTT reagent (5 mg/ml in phosphate buffered saline) was added to each well. After 2 h of incubation at 37° C., 200 µl of dimethylsulfoxide (DMSO) was added to each well to dissolve the formazan crystals. After 5 minutes, the optical absorbance was measured at 570 nm and converted to percent viability relative to control (untreated) cells. All samples were tested in quadruplicate.

In order to observe potential interaction of poly(ortho ester) nanoparticles with cells, both Müller and HEK-293 cells were selected to evaluate uptake of nanoparticles. Müller cells were selected due to their location within the retina of the eye and their potential influence when using poly(ortho ester) nanoparticles to deliver an intraocular therapy. HEK-293 cells were used to investigate if they display differential poly(ortho ester) nanoparticles uptake profiles. Cells were seeded in 24 well plates (BD Biosciences, Franklin Lakes, N.J.) 48 h before assays were initiated. Rhodamine 6G-loaded nanoparticles were diluted in culture medium to 0.2 and 1 mg/ml and added to monolayers of HEK-293 and Müller cells. The cells were then incubated at 37° C. for 2 h and 24 h. Cells were washed only once with phosphate buffered saline pH 7.4 and fixed in 1 ml of 1% paraformaldehyde solution (W/V) for 1 m, prior to labeling their nuclei with TO-PRO-3 IODIDE (Invitrogen; Grand Island, N.Y.) (1:2000) in phosphate buffered saline for 10 minutes. After washing cells with phosphate buffered saline, cell membranes were labeled with 10 µg/ml of OREGON GREEN 488 DHPE (Invitrogen; Grand Island, N.Y.) for 10 m and washed thoroughly three times with phosphate buffered saline. Cover slips were mounted on slides and images were taken on a confocal microscope (C1 Plus; Nikon, Tokyo, Japan).

Müller and HEK-293 cells were incubated with 0.2 and 1 mg/ml rhodamine 6G-loaded nanoparticles (20 µg of dye in 1 mg/ml nanoparticle emulsion) for 2 h and 24 h as described for use in confocal microscopy. The cells were washed once with 1 ml of fresh medium, then with phosphate buffered saline twice. Cells were permeabilized by freeze-thaw cycles. Both permeabilized cells and washings were lyophilized at 0.002 mbar, −50° C. for 24 h (Freezone, Labconco Corporation, Kansas, Mo.) and obtained powders were suspended in a 2 ml, 1:1 mixture of dimethylsulfoxide (DMSO) and deionized water (DIW). All samples were centrifuged at 20,000 rpm for 20 minutes. The clear supernatants were analyzed for rhodamine 6G at excitation/emission=528 nm/560 nm using a microplate reader (FLx800, BioTek Instruments, Winooski, Vt.). Linearity range of the calibration curve was between 2-10 µg/ml and the correlation coefficient of the calibration curve was 0.9996±0.0002. All samples were analyzed in triplicate.

Example 5

Novel Celecoxib-Loaded Poly(Ortho Ester) Nanoparticles

This example discloses the synthesis of novel celecoxib-loaded poly(ortho ester) nanoparticles, their physical characterization and cytocompatibility studies. Poly(ortho esters) are hydrophobic, biocompatible, and bioerodible polymers possessing superior characteristics. Drug release kinetics from poly(ortho ester), as well as polymer degradation rate follows zero-order kinetics without any burst effect. Furthermore, drug release can be controlled by factors such as polymer molecular weight and the physicochemical properties of the incorporated active substances (Heller, J. *Ocular delivery using poly(orthoesters), Advanced Drug Delivery Reviews,* 2005, 57, 2053-2062; Rothen-Weinhold, A.; Schwach-Abdellaoui, K.; Barr, J; Ng, S. Y; Shen, H. R.; Gurny, R.; Heller, J. *Release of BSA from poly(ortho ester) extruded thin strands, Jthenal of controlled Release,* 2001, 71, 31-37; Einmahl, S.; Behar-Cohen, F.; D'Hermies, F.; Rudaz, S.; Tabatabay, C.; Renard, G.; Gurny, R. *A new poly(ortho ester)-based drug delivery system as an adjunct treatment in filtering surgery, Investigative Ophthalmology and Visual science,* 2001, 42, 695-700). The main objective of this example was to develop biodegradable, non-toxic, poly(ortho ester) nanoparticles and assess their ability to provide sustained celecoxib delivery in a therapeutically effective concentration for at least three months.

Materials: 1,10 decanediol, D,L Lactone, poloxamer 188, 3-(4,5-Dimethylthiazol-2-yl)-2,5-diphenyltetrazolium bromide (MTT), Ethyl acetate and dimethylsulfoxide and the fluorescent dye Nile red were obtained from Sigma Aldrich (St. Louis, Mo.). 3,9-diviyl-2,4,8,10-tetraoxaspiro[5.5]undecane was obtained from AK Scientific Inc, USA. Lactate assay kit was purchased from Bio Vision. Ethyl acetate and dimethylsulfoxide (DMSO) were used as obtained. Dulbecco's Modified Eagle Medium was purchased from Fisher Scientific (Fair Lawn, N.J.). Oregon Green 488 DHPE and TO-PRO-3 IODIDE (Invitrogen; Grand Island, N.Y.) were purchased from Invitrogen (Grand Island, N.Y.). Human Embryonic Kidney cell lines (HEK 293), Eagle's minimal essential medium (EMEM), were obtained from ATCC (Manassas, Va.). rMC-1 Müller cells (Müller cells) were generously provided by Dr. Vijay Sarthy (Northwestern University). Poly(ortho ester) polymer was synthesized and characterized as described in the literature. (K. Schwach-Abdellaoui, J. Heller, R. Gurny, *Jthenal of Biomaterial Science Polymer Edn.* 1999, 10, 375).

Celecoxib-loaded poly(ortho ester) nanoparticles were prepared by an oil-in-water-in-water [(O/W)/W] double emulsion solvent diffusion technique with minor modifications (K. C. Song, H. S. Lee, I. Y. Choung, K. I. Cho, Y. Ahn, E. J. Choi, *Colloids and surfaces A: Physiochem. Eng. Aspects,* 2006, 276, 162). Briefly, poly(ortho ester) (90 mg) and celecoxib (60 mg) were dissolved in ethyl acetate (9 ml). The organic phase (18 ml) was added to an aqueous solution containing poloxamer 188 (1.25% w/v) and allowed to mutual saturation of ethyl acetate and water. The primary O/W emulsion was formed by sonication over an ice bath using a micro tip probe sonicator (Sonicator Model S-4000; Misonic, Inc., Newtown, Conn.) at 65% intensity for 4 m. To allow the diffusion of ethyl acetate into water, this primary emulsion was added drop wise to water (72 ml) to form [(O/W)/W] double emulsion under moderate magnetic stirring. The organic solvents were allowed to evaporate overnight by stirring on a magnetic stir plate. Nanoparticles thus formed were collected by ultracentrifugation (60,000 rpm, 2 h, 25° C.), and then washed three times with water to remove unincorporated celecoxib and poloxamer 188. The final product was dried by lyophilization for 48 h. Blank nanoparticles and Nile red loaded-nanoparticles were prepared in the same way mentioned above without celecoxib.

Particles were characterized by dynamic light scattering (DLS) and transmission electron microscopy (TEM). DLS measurements were conducted with 1 mg/ml of particle emulsions in Millipore water with a MALVERN NANO-ZS (Malvern Instruments, Worcestershire, UK). The morphology of poly(ortho ester) nanoparticles was observed using a transmission electron microscope (JEM-2000 EX II Electron Microscope, JEOL, LTD, Tokyo, Japan) using an acceleration voltage of 60 kV. Two microliters of poly(ortho ester) nanoparticles (0.5 mg/ml) were placed at the center of a copper grid and the grid was visualized under the electron microscope with appropriate magnification.

In vitro drug release: A stock solution of celecoxib was prepared for standard curve as described earlier (Saha, R. N.; Sajeev, C.; Jadhav, P. R.; Patil, S. P.; Srinivasan, N.; *Jthenal of Pharmaceutical and Biomedical Analysis*, 28, 2002, 741). The λ max of celecoxib in the above media was determined by scanning a suitable dilution of the stock. The encapsulation efficiency of celecoxib in the drug-loaded nanoparticles was determined by dissolving a powder of drug-loaded nanoparticles (10 mg) in 1:1 ratio of dimethylsulfoxide (DMSO): deionized water (DIW) (2 ml). Samples were rotated for at least 24 h at 50 rpm to ensure complete dissolution in aqueous dimethylsulfoxide (DMSO) solution. Blank nanoparticles were treated identically. The concentration of celecoxib in the resulting solution was determined by measuring the absorbance at 251 nm with a spectrophotometer (MQX 200, Bio-Tec Instruments, Vermont) and then subtracting the absorbance values from the blank nanoparticles. The linear range of the calibration curve was between 1-20 μg/ml and correlation coefficient was 0.999±0.00026. All samples were analyzed in triplicate.

Dialysis technique was adopted to carry out the release experiments. Celecoxib release profiles were determined by suspending drug-loaded nanoparticles (30 mg) in phosphate buffered saline (0.5 ml) at pH 7.4. Samples were incubated at 37° C. while shaking at 50 rpm in an incubator shaker (C 24, New Brunswick Scientific, N.J.). The released media was removed and replaced with fresh buffer. The concentration of celecoxib in the released media was determined using the UV detection method described above. The absorption of supernatant collected from blank nanoparticles was negligible at 251 nm throughout the release experiment. The amount of drug in each sample was summed with the amount at each previous time point to obtain the cumulative drug release amount and the total was divided by the amount of drug in the nanoparticles (encapsulation efficiency times mass of drug-loaded nanoparticles) to calculate the cumulative drug release percentage. Each release experiment was performed in triplicate. Lactic acid release from the poly(ortho ester) is a sign of the initiation of polymer erosion (K Schwach-Abdellaoui, J. Heller, R. Gurny, *Macromolecules*, 1999, 32, 301). Therefore, the quantification of lactic acid released from particles is essential to determine whether poly(ortho ester) nanoparticles eroding or not. Blank nanoparticles (30 mg) were suspended in phosphate buffered saline (0.5 ml) and dialyzed against fresh phosphate buffered saline (0.5 ml). Each day, lactic acid released medium was collected and replaced by fresh phosphate buffered saline and the amount of lactic acid released from nanoparticles was quantified in the release medium using lactate assay kit (BioVision Inc., California, USA).

In vitro cytotoxicity of poly(ortho ester) nanoparticles was evaluated by an MTT assay. HEK 293 cells were seeded (4400 cells/well) into each well of an opaque white 96-well plate and allowed to incubate overnight in humidified atmospheres (5% $CO_2$, 37° C.). One hundred microliters of diluted nanoparticles (0.1, 0.2, 0.3, 0.4, 0.5, 0.6, and 1 mg/ml) stock solution was added to each well and incubated with the cells for 48 h, and then replaced with growth medium (160 μl). MTT reagent (40 μl) was added to each well to form formazan. After 2 h of incubation at 37° C., 200 μl of dimethylsulfoxide (DMSO) was added to each well to dissolve the formazan crystals. After 5 m optical absorbance was measured at 570 nm and converted to percent viability relative to control (untreated) cells (n=4).

In order to observe poly(ortho ester) nanoparticles cell association, HEK 293 and Müller cells were seeded in 24 well plates (BD Biosciences, Franklin Lakes, N.J.) 48 h before assays were initiated. Nile red-loaded nanoparticles were diluted in culture media (0.2 and 1 mg/ml) and added to monolayers of HEK 293 and Müller cells. The cells were then incubated at 37° C. for 2 h and 24 h. Cells were washed only once with phosphate buffered saline pH 7.4 and fixed in 1% paraformaldehyde, prior to labeling their nuclei with TO-PRO-3 IODIDE (Invitrogen; Grand Island, N.Y.) (1:2000) in phosphate buffered saline for 10 m. After washing cells with phosphate buffered saline, cell membranes were labeled with Oregan 488 DHPE (10 μg/ml) for 10 m and washed thoroughly three times with phosphate buffered saline. Cover slips were mounted on slides and images were taken on a confocal microscope (C1 Plus; Nikon, Tokyo, Japan).

HEK 293 and Müller cells were incubated with Nile red-loaded nanoparticles (0.2 and 1 mg/ml) (20 μg of dye in 1 mg/ml nanoparticle emulsion) for 2 h and 24 h as described for use in confocal microscopy. Nile red was quantified in all washings and cell lysates according to the method mentioned in the literature (Kurejová, M.; Uhrik, B.; Sulová, Z.; Sedláková, B.; KrizanováO.; Lacinová, L.; *Europian Jthenal of Pharmacology*, 567, 2007, 10).

INCORPORATED BY REFERENCE

Patents, patent applications, and non-patent documents throughout this application are hereby expressly incorporated herein by reference.

The invention claimed is:
1. A composition comprising: a plurality of blank, biodegradable poly(ortho ester) nanoparticles comprising poly(ortho ester) and a latent acid at a molar ratio of 95:5 poly(ortho ester):latent acid, and a therapeutically effective amount of a bioactive agent encapsulated in the nanoparticles,
   wherein the nanoparticles have a polydispersity value of less than or equal to about 0.25, wherein the bioactive agent is selected from a hydrophilic molecule and a hydrophobic molecule, wherein the bioactive agent is released from the nanoparticles for at least 14 weeks with zero-order kinetics, and wherein the encapsulation efficiency of the hydrophilic molecule is at least about 20%.

2. The composition of claim 1, wherein the polydispersity value of the loaded poly(ortho ester) nanoparticles is lower than the polydispersity value of the blank poly(ortho ester) nanoparticles.

3. The composition of claim 1, wherein said bioactive agent is lipophilic and a polydispersity value of the loaded poly(ortho ester) nanoparticles is lower than or substantially similar to the polydispersity value of the blank poly(ortho ester) nanoparticles.

4. The composition of claim 1, further comprising a pharmaceutically acceptable carrier.

5. The composition of claim 1, in which the bioactive agent is a multivalent N-linked glycan.

6. The composition of claim 5, in which the N-linked glycan is an asialo, galactosylated, biantennary (NA2) oligosaccharide.

7. The composition of claim 5, in which the N-linked glycan is an asialo, galactosylated triantennary (NA3) oligosaccharide.

8. The composition of claim 2, further comprising a nanoparticle stabilizer.

9. The composition of claim 1, wherein the latent acid is lactic acid.

10. The composition of claim 2 wherein the bioactive agent is a lipophilic bioactive agent.

11. The composition of claim 10 wherein the average diameter of the loaded poly(ortho ester) nanoparticles ranges from about 151-165 nm.

12. The composition of claim 10 wherein the bioactive agent is selected from the group consisting of celecoxib and nile red.

13. The composition of claim 1 wherein the bioactive agent is a hydrophilic bioactive agent.

14. The composition of claim 13 wherein the bioactive agent the average diameter of the loaded poly(ortho ester) nanoparticles ranges from about 241 to 298 nm.

15. The composition of claim 13 wherein the bio active agent is selected from the group consisting of: epinephrine, rhodamine 6G and bovine serum albumin (BSA).

16. A poly(ortho ester) nanoparticle bioactive agent delivery product made by the process comprising the steps of: (a) dissolving a hydrophilic bioactive agent in water to form an aqueous solution, (b) dissolving poly(ortho ester) in an organic solution, (c) adding the aqueous solution to the organic solution of poly(ortho ester) to form an admixture; (d) sonicating the admixture to form a water-in-oil emulsion, (e) adding the water-in-oil emulsion to an aqueous phase containing an emulsifying agent to obtain a double emulsion (f) evaporating the organic solvent to form a plurality of solidified nanoparticles, each of said nanoparticles having a diameter of less than 1000 nm, wherein the poly(ortho ester) nanoparticle comprises poly(ortho ester) and a latent acid at a molar ratio of 95:5 poly(ortho ester):latent acid.

17. The product of claim 16 wherein the encapsulation efficiency is at least 20 percent.

18. The product of claim 16 wherein the average diameter of the plurality of loaded poly(ortho ester) nanoparticles ranges from about 241 to 298 nm.

19. A poly(ortho ester) nanoparticle bioactive agent delivery product made by the process comprising the steps of (a) dissolving poly(ortho ester) and a lipophilic bioactive agent in an organic solution to form a mixture (b) separating an organic phase from the mixture (c) adding an emulsifying agent to the organic phase, (c) emulsifying the organic phase to form an emulsion (d) diffusing the organic solvent from the emulsion to form a plurality of lipophilic bioactive agent loaded poly(ortho ester) nanoparticles, each of said nanoparticles having a diameter of less than 1000 nm, wherein the poly(ortho ester) nanoparticle comprises poly(ortho ester) and a latent acid at a molar ratio of 95:5 poly(ortho ester):latent acid.

20. The product of claim 19 wherein the encapsulation efficiency is at least 98%.

21. The product of claim 19 wherein the average diameter of the plurality of loaded poly(ortho ester) nanoparticles ranges from about 151-165 nm.

22. A sustained release delivery system for treatment of an ocular condition comprising;
a poly(ortho ester) nanoparticle formulated with an therapeutically effective amount of a bioactive agent sufficient to deliver the bioactive agent with zero-order kinetics for at least 14 weeks, wherein the poly(ortho ester) nanoparticle comprises poly(ortho ester) and a latent acid at a molar ratio of 95:5 poly(ortho ester):latent acid, and
wherein the polydispersity value of the nanoparticle is less than or equal to about 0.25, wherein the bioactive agent is selected from a group consisting of a hydrophilic molecule and a hydrophobic molecule, and wherein the encapsulation efficiency of the bioactive agent is at least about 20%.

23. The composition of claim 1, wherein the nanoparticles have low cytotoxicity with concentrations of the nanoparticles at less than or equal to about 1 mg/ml.

24. The composition of claim 1, wherein the encapsulation efficiency of the nanoparticles is at least about 60%.

25. The composition of claim 1, wherein the encapsulation efficiency of the bioactive agent in the nanoparticles is at least about 98%.

26. The composition of claim 1, wherein the polydispersity value of the nanoparticles is less than or equal to 0.19.

27. The composition of claim 1, wherein the average diameter of the nanoparticles ranges from about 151-165 nm.

28. The composition of claim 1, wherein the average diameter of the nanoparticles ranges from about 241 to 298 nm.

* * * * *